United States Patent
Tucker et al.

(10) Patent No.: US 12,043,865 B2
(45) Date of Patent: Jul. 23, 2024

(54) GENETIC PROBE FOR THE DETECTION OF A SINGLE NUCLEOTIDE POLYMORPHISM (SNP) OR A SINGLE NUCLEOTIDE MODIFICATION OF A TARGET NUCLEIC ACID

(71) Applicant: The University of Birmingham, Birmingham (GB)

(72) Inventors: James Tucker, Birmingham (GB); Zoe Pikramenou, Birmingham (GB); Andrew Beggs, Birmingham (GB); Zsusa Nagy, Birmingham (GB); Purbani Chakrabarti, Birmingham (GB)

(73) Assignee: The University of Birmingham, Birmingham (GB)

( * ) Notice: Subject to any disclaimer, the term of this patent is extended or adjusted under 35 U.S.C. 154(b) by 587 days.

(21) Appl. No.: 16/643,133

(22) PCT Filed: Aug. 9, 2018

(86) PCT No.: PCT/GB2018/052275
§ 371 (c)(1),
(2) Date: Feb. 28, 2020

(87) PCT Pub. No.: WO2019/043353
PCT Pub. Date: Mar. 7, 2019

(65) Prior Publication Data
US 2020/0332349 A1    Oct. 22, 2020

(30) Foreign Application Priority Data
Sep. 1, 2017   (GB) .................... 1714068

(51) Int. Cl.
C07H 21/02     (2006.01)
C12Q 1/6827    (2018.01)
C12Q 1/6876    (2018.01)

(52) U.S. Cl.
CPC .......... C12Q 1/6827 (2013.01); C12Q 1/6876 (2013.01); C12Q 2563/107 (2013.01); C12Q 2563/113 (2013.01); C12Q 2563/155 (2013.01)

(58) Field of Classification Search
CPC ....... C12Q 1/68; C12Q 1/6827; C12Q 1/6876
See application file for complete search history.

(56) References Cited

U.S. PATENT DOCUMENTS 5,451,463 A * 9/1995 Nelson .................. C07H 21/00
                                                    428/402
2014/0248612 A1* 9/2014 Princen ................ C12Q 1/6851
                                                    435/6.11

FOREIGN PATENT DOCUMENTS

CN    102220431 A1    10/2011
WO    2011029835 A2    3/2011

OTHER PUBLICATIONS

Kershaw, Nanoparticle bound nucleic acid probes for DNA detection and gene inactivation, Doctor of Philosophy Thesis, College of Engineering and Physical Science, University of Birmingham, Sep. 2016. (Year: 2016).*

(Continued)

Primary Examiner — Frank W Lu
(74) Attorney, Agent, or Firm — NIXON PEABODY LLP; Mark J. Fitzgerald; Nicole D. Kling

(57) ABSTRACT

The present invention relates to a genetic probe comprising:
a nanoparticle;
an oligonucleotide probe anchored to the surface of the nanoparticle, comprising an oligonucleotide backbone with a tag incorporated therein via a linker group; and (Continued)

a reference probe anchored to the surface of the nanoparticle, wherein the reference probe comprises a marker; wherein either (a) the tag is an organic fluorescent tag and the marker is a transition metal-based fluorescent marker; or (b) the tag is a redox-active tag and the marker is a transition metal-based redox-active marker. The invention also relates to a composition or kit containing a probe of the invention.

7 Claims, 12 Drawing Sheets

Specification includes a Sequence Listing.

(56) References Cited

OTHER PUBLICATIONS

Duprey et al., Macrocyclic metal complex-DNA conjugates for electrochemical sensing of single nucleobase changes in DNA, J. Am. Chem. Soc., 2016, 138, 746-749. (Year: 2016).*

Song et al., Gold-nanoparticle-based multicolor nanobeacons for sequence-speific DNA analysis, Angew. Chem. Int. Ed., 2009, 48, 8670-8674. (Year: 2009).*

Duprey et al., Anthracene-modified oligonucleotides as fluorescent DNA mismatch sensors: discrimination between various base-pair mismatches, Supramolecular Chemistry, 2011, 23, 3-4, 273-277. (Year: 2011).*

Wang et al., A pilot study of noninvasive prenatal diagnosis of alpha- and beta-thalassemia with target capture sequencing of cell-free fetal DNA in maternal blood, Genetic Testing and Molecular Biomarkers, 2017, 21, 7, 433-439. (Year: 2017).*

Notification Concerning Transmittal of International Preliminary Report on Patentability. Issued in International Application No. PCT/GB2018/052275 dated Mar. 3, 2020. 9 pages.

Duprey et al. "Single site discrimination of cytosine, 5-methylcytosine, and 5-hydroxymethylcytosine in target DNA using anthracene-tagged fluorescent probes." ACS Chemical Biology 11(3): 717-721 (2016), 5 pages.

Moran et al. "Detection of a single DNA base-pair mismatch using an anthracene-tagged fluorescent probe." Chemical Communications 48: 5003-5005 (2006), 3 pages.

Wang et al. "A dynamic sandwich assay on magnetic beads for selective detection of single-nucleotide mutations at room temperature." Biosensors and Bioelectronics 94: 305-311 (2017), 7 pages.

Zhang et al. "Electrochemiluminescence ratiometry: a new approach to DNA biosensing." Analytical Chemistry 85(11): 5321-5325 (2013), 5 pages.

Zhao et al. "Detection of single nucleotide polymorphisms within a sequence of a gene associated with prostate cancer using a fluorophore-tagged DNA probe." Bioorganic & Medicinal Chemistry Letters 22(1): 129-132 (2012), 4 pages.

Liguo et al. "The Construction and Application of Ratiometric Fluorescent Probes" China Academic Journal Electronic Publishing House. 43(18): 90-91 (2016) [English Abstract Provided].

* cited by examiner

AuNP-A

AuNP-B

Figure 13:
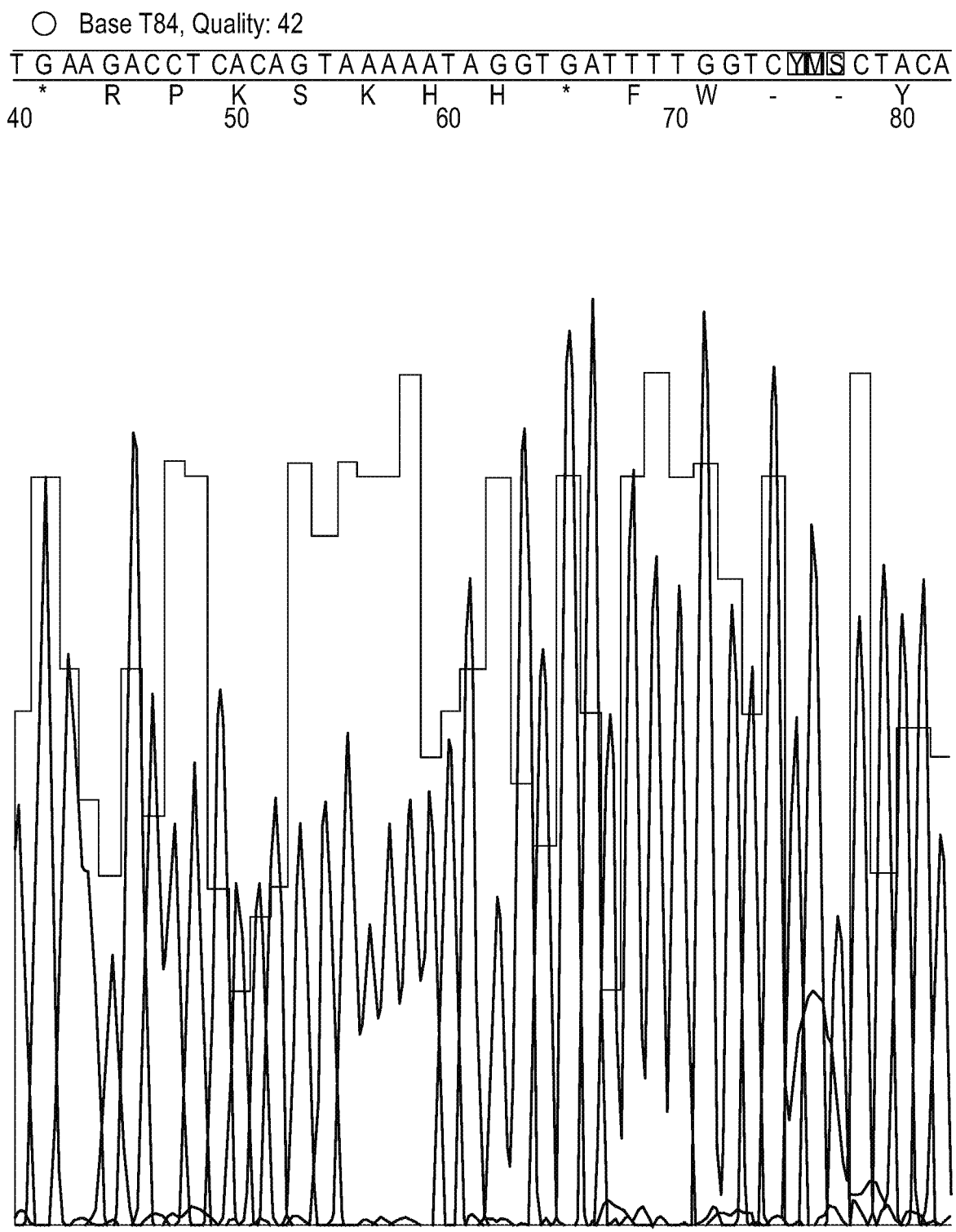

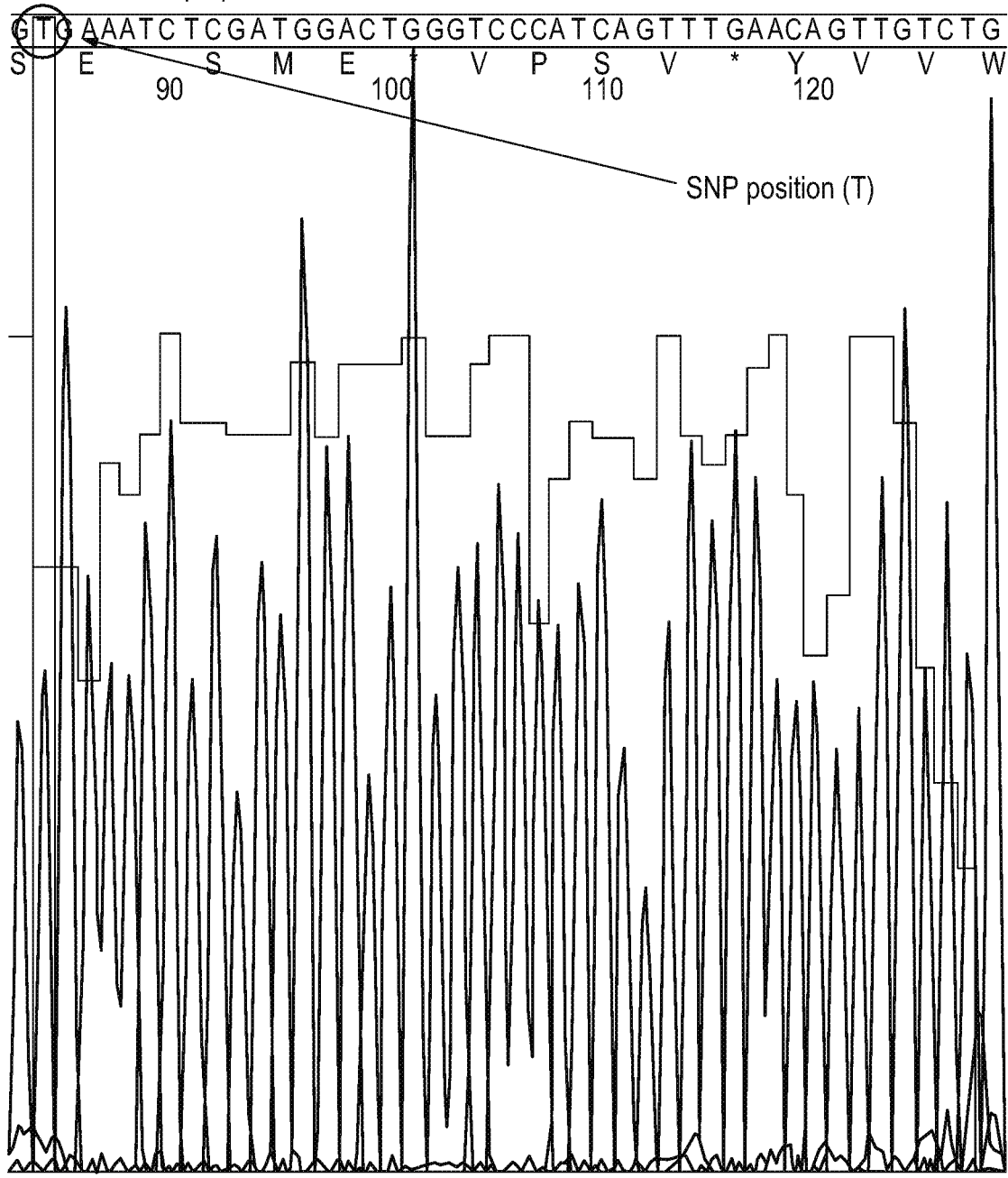
Figure 13 Contiuned

Figure 14:
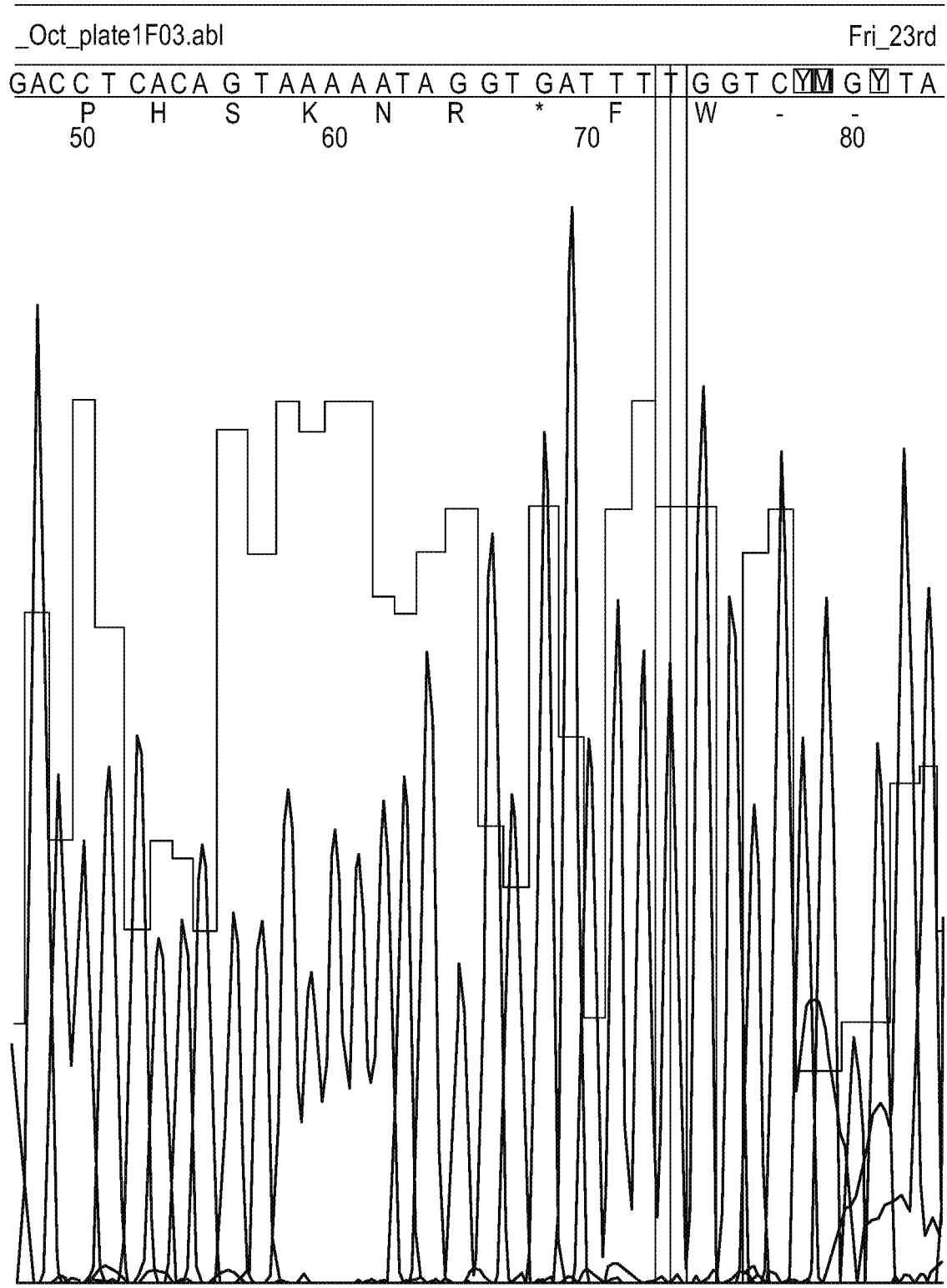

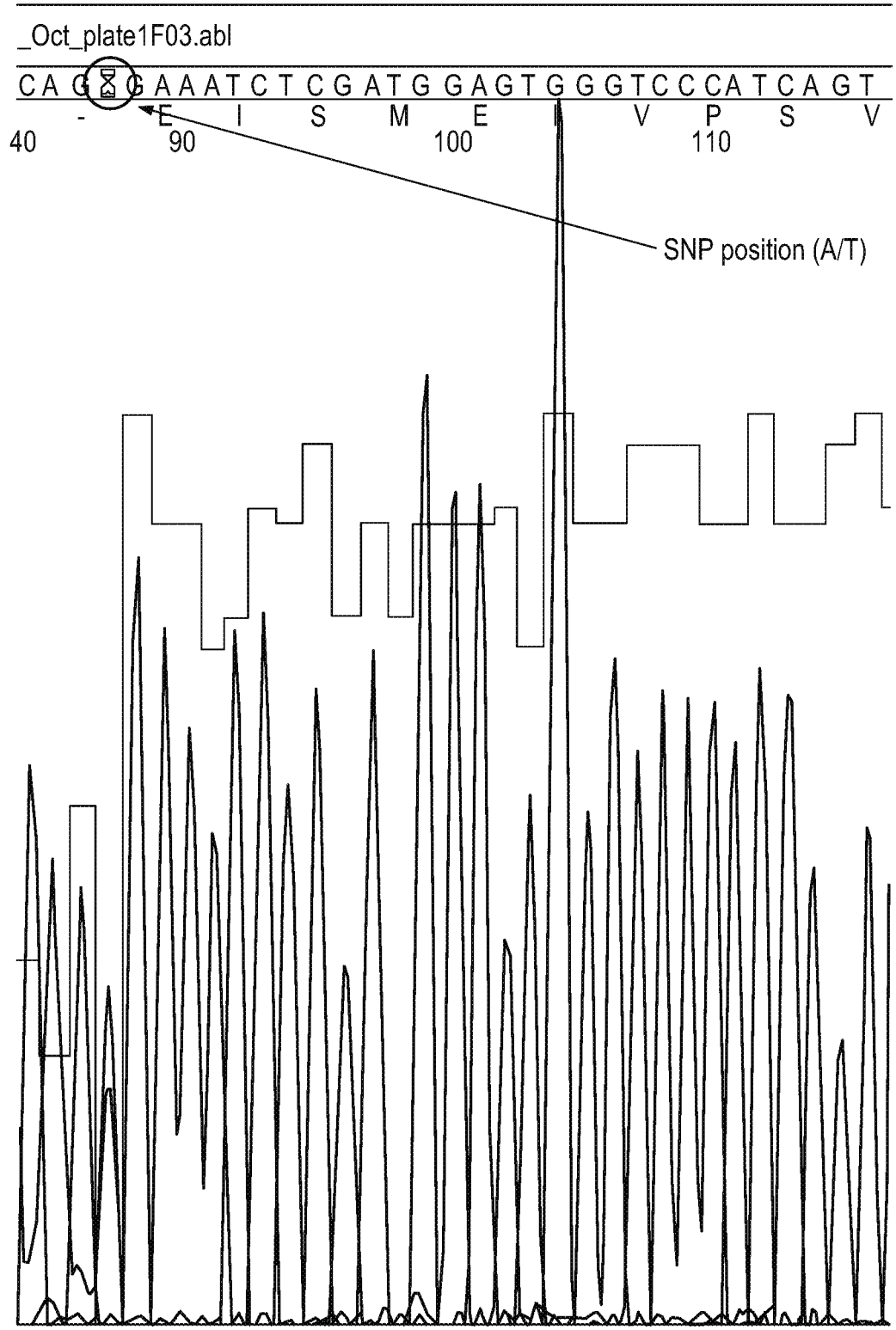
Figure 14 Contiuned

SEQUENCE LISTING

```
<160> NUMBER OF SEQ ID NOS: 20

<210> SEQ ID NO 1
<211> LENGTH: 15
<212> TYPE: DNA
<213> ORGANISM: Artificial Sequence
<220> FEATURE:
<223> OTHER INFORMATION: probe
<220> FEATURE:
<221> NAME/KEY: tagged linker
<222> LOCATION: (8)..(8)
<223> OTHER INFORMATION: tagged linker
<220> FEATURE:
<221> NAME/KEY: misc_feature
<222> LOCATION: (8)..(8)
<223> OTHER INFORMATION: n is a, c, g, or t
```

-continued

<400> SEQUENCE: 1
agtcgcgnct cagct                                                         15

<210> SEQ ID NO 2
<211> LENGTH: 15
<212> TYPE: DNA
<213> ORGANISM: Artificial Sequence
<220> FEATURE:
<223> OTHER INFORMATION: probe
<220> FEATURE:
<221> NAME/KEY: tagged linker or SNP
<222> LOCATION: (8)..(8)
<223> OTHER INFORMATION: tagged linker or SNP
<220> FEATURE:
<221> NAME/KEY: misc_feature
<222> LOCATION: (8)..(8)
<223> OTHER INFORMATION: n is a, c, g, or t

<400> SEQUENCE: 2
agatttcnct gtagc                                                         15

<210> SEQ ID NO 3
<211> LENGTH: 15
<212> TYPE: DNA
<213> ORGANISM: Artificial Sequence
<220> FEATURE:
<223> OTHER INFORMATION: probe

<400> SEQUENCE: 3
tggactctct caatg                                                         15

<210> SEQ ID NO 4
<211> LENGTH: 16
<212> TYPE: DNA
<213> ORGANISM: Artificial Sequence
<220> FEATURE:
<223> OTHER INFORMATION: probe
<220> FEATURE:
<221> NAME/KEY: thioctic acid modification
<222> LOCATION: (1)..(1)
<223> OTHER INFORMATION: thioctic acid modification
<220> FEATURE:
<221> NAME/KEY: misc_feature
<222> LOCATION: (1)..(1)
<223> OTHER INFORMATION: n is a, c, g, or t

<400> SEQUENCE: 4
ntggactctc tcaatg                                                        16

<210> SEQ ID NO 5
<211> LENGTH: 16
<212> TYPE: DNA
<213> ORGANISM: Artificial Sequence
<220> FEATURE:
<223> OTHER INFORMATION: probe
<220> FEATURE:
<221> NAME/KEY: thioctic acid modification
<222> LOCATION: (1)..(1)
<223> OTHER INFORMATION: thioctic acid modification
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: 1L anthracine modification
<222> LOCATION: (9)..(9)

```
<223> OTHER INFORMATION: 1L anthracine modification
<220> FEATURE:
<221> NAME/KEY: misc_feature
<222> LOCATION: (9)

```
<222> LOCATION: (1)..(1)
<223> OTHER INFORMATION: thioctic acid modification
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: 1L anthracene probe
<222> LOCATION: (14)..(14)
<223> OTHER INFORMATION: 1L anthracene probe
<220> FEATURE:
<221> NAME/KEY: misc_feature
<222> LOCATION: (14)..(14)
<223> OTHER INFORMATION: n is a, c, g, or t

<400> SEQUENCE: 8
naaaaatgga ctcnctcaat g                                          21

<210> SEQ ID NO 9
<211> LENGTH: 26
<212> TYPE: DNA
<213> ORGANISM: Artificial Sequence
<220> FEATURE:
<223> OTHER INFORMATION: probe
<220> FEATURE:
<221> NAME/KEY: thioctic acid modification
<222> LOCATION: (1)..(1)
<223> OTHER INFORMATION: thioctic acid modification
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: 1L anthracene probe
<222> LOCATION: (19)..(19)
<223> OTHER INFORMATION: 1L anthracene probe
<220> FEATURE:
<221> NAME/KEY: misc_feature
<222> LOCATION: (19)..(19)
<223> OTHER INFORMATION: n is a, c, g, or t

<400> SEQUENCE: 9
naaaaaaaaa atggactcnc tcaatg                                     26

<210> SEQ ID NO 10
<211> LENGTH: 15
<212> TYPE: DNA
<213> ORGANISM: Artificial Sequence
<220> FEATURE:
<223> OTHER INFORMATION: probe

<400> SEQUENCE: 10
cattgagaga gtcca                                                 15

<210> SEQ ID NO 11
<211> LENGTH: 15
<212> TYPE: DNA
<213> ORGANISM: Artificial Sequence
<220> FEATURE:
<223> OTHER INFORMATION: probe

<400> SEQUENCE: 11
cattgagaaa gtcca                                                 15

<210> SEQ ID NO 12
<211> LENGTH: 15
<212> TYPE: RNA
<213> ORGANISM: Artificial Sequence
<220> FEATURE:
<223> OTHER INFORMATION: probe
```

```
<400> SEQUENCE: 12
cauugagaga gucca                                                    15

<210> SEQ ID NO 13
<211> LENGTH: 15
<212> TYPE: RNA
<213> ORGANISM: Artificial Sequence
<220> FEATURE:
<223> OTHER INFORMATION: probe

<400> SEQUENCE: 13
cauugagaaa gucca                                                    15

<210> SEQ ID NO 14
<211> LENGTH: 15
<212> TYPE: DNA
<213> ORGANISM: Artificial Sequence
<220> FEATURE:
<223> OTHER INFORMATION: probe

<400> SEQUENCE: 14
agctgagacg cgact                                                    15

<210> SEQ ID NO 15
<211> LENGTH: 15
<212> TYPE: DNA
<213> ORGANISM: Artificial Sequence
<220> FEATURE:
<223> OTHER INFORMATION: probe

<400> SEQUENCE: 15
agctgagccg cgact                                                    15

<210> SEQ ID NO 16
<211> LENGTH: 20
<212> TYPE: RNA
<213> ORGANISM: Artificial Sequence
<220> FEATURE:
<223> OTHER INFORMATION: probe
<220> FEATURE:
<221> NAME/KEY: compound 8 modification
<222> LOCATION: (1)..(1)
<223> OTHER INFORMATION: compound 8 modification
<220> FEATURE:
<221> NAME/KEY: misc_feature
<222> LOCATION: (1)..(1)
<223> OTHER INFORMATION: n is a, c, g, or u

<400> SEQUENCE: 16
ncaaucaggg ucgacgagaa                                               20

<210> SEQ ID NO 17
<211> LENGTH: 19
<212> TYPE: RNA
<213> ORGANISM: Artificial Sequence
<220> FEATURE:
<223> OTHER INFORMATION: probe

<400> SEQUENCE: 17
uucucgucga cccugauug                                                19

<210> SEQ ID NO 18
<211> LENGTH: 15
<212> TYPE: RNA
<213> ORGANISM: Homo sapiens
<220> FEATURE:
<221> NAME/KEY: SNP
```

```
<222> LOCATION: (8)..(8)
<223> OTHER INFORMATION: any nucletide
<220> FEATURE:
<221> NAME/KEY: misc_feature
<222> LOCATION: (8)..(8)
<223> OTHER INFORMATION: n is a, c, g, or u

<400> SEQUENCE: 18
ucagcgcnga gucga                                                    15

<210> SEQ ID NO 19
<211> LENGTH: 15
<212> TYPE: DNA
<213> ORGANISM: Homo sapiens
<220> FEATURE:
<221> NAME/KEY: SNP
<222> LOCATION: (8)..(8)
<223> OTHER INFORMATION: any nucleotide
<220> FEATURE:
<221> NAME/KEY: misc_feature
<222> LOCATION: (8)..(8)
<223> OTHER INFORMATION: n is a, c, g, or t

<400> SEQUENCE: 19
tcagcgcnga gtcga                                                    15

<210> SEQ ID NO 20
<211> LENGTH: 15
<212> TYPE: DNA
<213> ORGANISM: Homo sapiens
<220> FEATURE:
<221> NAME/KEY: SNP
<222> LOCATION: (8)..(8)
<223> OTHER INFORMATION: any nucleotide
<220> FEATURE:
<221> NAME/KEY: misc_feature
<222> LOCATION: (8)..(8)
<223> OTHER INFORMATION: n is a, c, g, or t

<400> SEQUENCE: 20
tctaaagnga catcg                                                    15
```

GENETIC PROBE FOR THE DETECTION OF A SINGLE NUCLEOTIDE POLYMORPHISM (SNP) OR A SINGLE NUCLEOTIDE MODIFICATION OF A TARGET NUCLEIC ACID

CROSS REFERENCE TO RELATED APPLICATIONS

This Application is a U.S. National Phase Entry of International Patent Application No. PCT/GB2018/052275 filed on Aug. 9, 2018, which claims the benefit under 35 U.S.C. § 119(b) of GB Application Serial No: 1714068.2 filed on filed Sep. 1, 2017, the contents of which are incorporated herein in their entirety by reference.

This invention relates to a genetic probe for the detection of a single nucleotide polymorphism (SNP) or single nucleotide modification of a target nucleic acid, and methods of determining the percentage of single nucleotide polymorphisms (SNPs) or single nucleotide modifications of a target nucleic acid in a pool of the target nucleic acid.

SEQUENCE LISTING

The instant application contains a Sequence Listing which has been submitted electronically in ASCII format and is hereby incorporated by reference in its entirety. Said ASCII copy, created on Jul. 28, 2023 is named 052342-097000US-PX.txt and is 6451 bytes in size.

BACKGROUND TO THE INVENTION

Single Nucleotide Polymorphisms (SNPs), variations in one nucleobase at one site in a particular sequence of genomic DNA, play an important role in the development and prognosis of diseases with a genetic component, including cancer. In clinical research, surgery and diagnostics, there is a need for a method that gives a rapid, cheap and reliable read-out out of the allelic (i.e. SNP) ratio to inform clinical decision making.

Several commercial assays for identifying the SNP composition are known, e.g. TaqMan. However although heterozygous alleles (i.e. samples from two copies of DNA that contain both SNP variants) can be readily distinguished from their homozygous counterparts (i.e. two identical copies), it is still difficult to quantify samples containing a non-50/50 ratio of the nucleobases. Such a situation could arise in regions of cancerous tissue, where the extent of a mutation (which would inform the amount of tissue to remove through surgery) is unknown. Or it could arise in heterozygous mRNA transcripts, where both copies of DNA are transcribed, but one more than another; such a situation could signify a misregulation in transcription associated with a particular disease.

SNP sensing methodology has recently been developed in which SNP identities can be read-out routinely from target samples of DNA (see Duprey, et al., ACS Chem. Biol., 2016, 11, 717-721; Zhao, et al., Biorg. Med. Chem. Lett., 2012, 22, 129; Duprey et al., Chem. Commun, 2011, 47, 6629; and Li et al., Anal. Chem., 2016, 88, 883-889). As with numerous other methods, including commercial ones, this approach uses duplex formation (hybridisation), involving a tagged DNA probe to generate a fluorescent signal. However one difference in this approach is that analysis is based on the strength of the signal generated (i.e. signal intensity) upon duplex formation, not on how well the duplex forms to give a signal. This means the assay can be done at room temperature and obviates the need to use narrow temperature windows to ensure only one transcript (or transcript product) binds. The sensing signal comes from the fluorescence emission from an anthracene tag on the probe strand either increasing or decreasing at a particular monitoring wavelength (e.g. 426 nm) upon duplex formation, with the intensity of the signal directly depending on the identity of the base opposite (See FIG. 1).

Duprey et al. (ACS Chem. Biol., 2016, 11, 717-721) have also demonstrated that the hybridization SNP sensing methodology can also discern base modifications (e.g. methylation of cytosine or oxidation of guanine) as well as base changes.

An aim of the present invention is to provide improved SNP sensing methodology and the provision of improved probes for such SNP sensing.

SUMMARY OF THE INVENTION

According to a first aspect of the invention, there is provided a genetic probe for the detection of a single nucleotide polymorphism (SNP) or a single nucleotide modification of a target nucleic acid, the genetic probe comprising:
 a nanoparticle;
 an oligonucleotide probe anchored to the surface of the nanoparticle, comprising an oligonucleotide backbone with a tag incorporated therein via a linker group; and
 a reference probe anchored to the surface of the nanoparticle, wherein the reference probe comprises a marker;
 wherein either (a) the tag is an organic fluorescent tag and the marker is a transition metal-based fluorescent marker; or (b) the tag is a redox-active tag and the marker is a transition metal-based redox-active marker.

The tag is suitably capable of partial insertion and stacking between adjacent base pairs of double-stranded oligonucleotides.

The marker is suitably not capable of partial insertion and stacking between adjacent base pairs of double-stranded oligonucleotides.

It will be appreciated that although the worked examples of the present application make use of the embodiment (a) that uses fluorescence, the invention can likewise be put into effect using the embodiment (b) that uses an electrochemical signal.

There is also provided, in another aspect, a composition that comprises a plurality of genetic probes according to first aspect of the invention. This may comprise two or more, or five or more, or ten or more, or fifty or more, or 100 or more, genetic probes according to first aspect of the invention.

The composition may be a solution or suspension. A solution of the genetic probes may have a concentration of at least 0.1 nM, at least 0.5 nM, at least 1 nM or at least 5 nM. The composition may comprise the plurality of genetic probes in an aqueous medium, e.g. a buffer.

The composition may comprise one or more additional substances such as polymers, solvents, biological fluids, proteins, surfactants and stabilisers. In some embodiments, the composition comprises polyacrylamide, an anionic surfactant (e.g. a fluorinated surfactant such as Zonyl® FSA), bovine serum albumin (BSA) and/or serum (e.g. human serum or foetal calf serum). Polyacrylamide enables the nanoparticles to be dried and re-suspended.

In some embodiments, the composition comprises polyacrylamide. The polyacrylamide may be prepared as a solution (e.g. 1 mg/ml aqueous solution), which is added to the composition comprising the nanoparticles in the amount required (e.g. 0.1 to 1% v/v).

In some embodiments, the composition comprises an anionic surfactant (e.g. Zonyl® FSA). The concentration of the anionic surfactant may be from 0.01 to 0.1% (v/v).

In some embodiments, the composition comprises serum (e.g. human serum or foetal calf serum). The concentration of the serum may be from 0.2% to 2% (v/v).

In some embodiments, the composition comprises bovine serum albumin (BSA). The BSA may be prepared as a solution (e.g. 1 mg/ml aqueous solution), which is added to the composition comprising the nanoparticles in the amount required (e.g. 0.1 to 1% v/v).

The genetic probe of the invention provides a quick, cheap and quantitative assessment for heterozygous nucleic acid samples that can accurately determine allelic ratios, either from DNA samples (for example in those arising from regions of cancerous tissue) or from mRNA transcripts.

The oligonucleotide backbone forms a duplex with the target strand of interest. It can be designed to be complementary to the target strand. Single base variations can be detected through changes in the emission intensity of the organic fluorescent tag.

The present invention allows ratiometric sensing, whereby the sensing signal from two separate fluorophores at two distinct wavelengths is analysed. Dividing one signal intensity by another obviates the need to determine the initial probe concentration; this both simplifies and facilitates the sensing process, in particular for analysis in cellular environments where probe concentrations would be difficult to determine. In a similar manner, in the electrochemical embodiment of the invention the electrical current (or charge generated) signal from two separate redox-active materials can analysed.

The present invention permits a ratiometric system which allows the detection of different SNP variants without the requirement for a baseline emission level for each experiment. Upon synthesising a new batch of the genetic probe of the invention, a ratio of the fluorescent tag to transition metal-based fluorescent marker signal can be measured and this ratio can then be used for all subsequent experiments using this batch. If the ratio when normalised doubles then the mismatching CA base pair is present; however if the ratio halves, then the matching CG base pair is present. Likewise, a ratio of the electrical current (or charge generated) signal from the redox-active tag to the electrical current (or charge generated) signal from the redox-active marker can be calculated and used.

Not requiring a baseline emission level for each experiment overcomes the problem of being able to only take a single measurement of the anthracene emission when detecting SNP targets within cells. The ratiometric sensing approach provided by the present invention also overcomes the problem of the variation in cell uptake of the probe. As long as there is surplus target to probe, the ratio of the tag signal to marker signal measured will give an accurate reading for what SNP is present in each cell.

Although ratiometric sensing is not new per se, the provision of the first probe and the second (standard/reference) probe in a form where they are separately mounted on a nanoparticle is new. This is advantageous because it provides a stable environment where the two probes are provided together, and there is certainty that the concentrations of the two probes in the test environment is identical, but additionally the second probe does not interact with the first probe and thus does not fluctuate in its emission/signal upon the first probe hybridising with the different targets.

In contrast, prior attempts at ratiometric sensing with fluorophores have encountered problems with the emission of the second fluorophore fluctuating considerably upon binding to the targets.

The genetic probe of the present invention is therefore beneficial in that it can be used to give a reliable concentration-independent emission/signal level of the first probe.

A further benefit of the genetic probe of the invention is that it is able to quantify samples containing a non-50/50 ratio of the nucleobases.

Advantageously, the genetic probe of the invention is readily taken up by cells without the need for chemical transfection.

It is known that the emission of an organic fluorophore when placed near a metallic nanoparticle is greatly reduced, up to 99.8%. See Dulkeith, E. et al. *Nano Lett.* 5, 585-9 (2005). The present invention goes against the teachings of the art, by permitting use of an organic fluorescent tag mounted on a metallic nanoparticle.

According to another aspect of the invention, there is provided a method of determining the percentage of single nucleotide polymorphisms (SNPs) or single nucleotide modifications of a target nucleic acid in a pool of the target nucleic acid, the method comprising:

contacting the pool of target nucleic acid with an oligonucleotide probe capable of detecting the SNP or single nucleotide modification, wherein the oligonucleotide probe is substantially complimentary to the target polynucleotide, and wherein the oligonucleotide probe comprises an oligonucleotide backbone with a tag incorporated therein via a linker group, wherein either the tag is an organic fluorescent tag or a redox-active tag, and wherein the tag is in a position that is arranged to be paired with a nucleotide of the target nucleic acid to be interrogated, whereby (i) the light emission of the organic fluorescent tag differs in intensity depending on the nucleotide's identity or modified structure; or (ii) the electrical charge of the redox-active tag differs in intensity depending on the nucleotide's identity or modified structure;

detecting the percentage change in the fluorescent emission intensity of the organic fluorescent tag when the pool of target nucleic acid is contacted by the oligonucleotide probe comprising the organic fluorescent tag, or detecting the percentage change in electrical charge intensity of the redox-active tag when the pool of target nucleic acid is contacted by the oligonucleotide probe comprising the redox-active tag; and determining the percentage of single nucleotide polymorphisms (SNPs) or single nucleotide modifications by comparing the percentage change in intensity of the tag to a calibration value that has been determined by linear regression of the percentage change in intensity of known standards.

Advantageously, studies on DNA and RNA sequences has revealed a surprisingly linear dependence in the emission signal intensity of the organic fluorescent tag or electrical charge intensity of the redox-active tag as a function of the SNP/ratio in the target in a sample, thus allowing the SNP ratio (i.e. allelic ratio) to be calibrated and then read-out for unknown mixtures through a simple measure of the emission intensity at a given wavelength or the electrical charge intensity of the redox-active tag. The method provides a rapid, cheap and reliable read-out out of the allelic (i.e. SNP) ratio to inform clinical decision making. The DNA sequence can be targeted or, where appropriate, mRNA transcripts analysed indirectly (e.g. via cDNA formation and then PCR amplification) or directly if enough target were present (e.g. mRNA detection in cells).

In one embodiment the tag is the organic fluorescent tag, and the light emission of the organic fluorescent tag differs in intensity depending on the nucleotide's identity or modified structure. In another embodiment the tag is the redox-active tag and the electrical charge of the redox-active tag differs in intensity depending on the nucleotide's identity or modified structure.

The oligonucleotide probe of the method of the invention may be part of, or consist of the genetic probe according to the invention described herein. The oligonucleotide probe of the method of the invention may comprise the same oligonucleotide probe as provided in the genetic probe according to the invention herein. In particular, embodiments of one aspect of the invention may be equally applied to equivalent embodiments of another aspect of the invention herein.

According to another aspect of the invention, there is provided a method of determining the percentage of single nucleotide polymorphisms (SNPs) or single nucleotide modifications of a target nucleic acid in a pool of the target nucleic acid, the method comprising:
  contacting the pool of target nucleic acid with the genetic probe according to the invention herein, which is capable of detecting the SNP or single nucleotide modification,
  detecting the percentage change in the fluorescent emission intensity of the organic fluorescent tag when the pool of target nucleic acid is contacted by the oligonucleotide probe comprising the organic fluorescent tag, or detecting the percentage change in electrical charge intensity of the redox-active tag when the pool of target nucleic acid is contacted by the oligonucleotide probe comprising the redox-active tag; and
  determining the percentage of single nucleotide polymorphisms (SNPs) or single nucleotide modifications by comparing the percentage change in intensity of the tag to a calibration value that has been determined by linear regression of the percentage change in intensity of known standards.

Detecting the percentage change in emission of the fluorescent tag when the pool of target nucleic acid is contacted by the oligonucleotide probe may comprise detecting the change in emission of the fluorescent tag upon hybridisation of the oligonucleotide probe to the target nucleic acid. The hybridisation of the nucleic acid probe with the target nucleic acid sequence may be detected by detecting the emission or change in emission intensity from the fluorescent tag and/or from the reference probe. Florescence emissions may be detected and measured by fluorescence spectroscopy, for example by a Shimadzu RF-5301 PC Spectrofluorophotometer.

Detecting the percentage change in electrical charge intensity of the redox-active tag when the pool of target nucleic acid is contacted by the oligonucleotide probe comprising the redox-active tag may comprise detecting the change in electrical charge intensity of the redox-active tag upon hybridisation of the oligonucleotide probe to the target nucleic acid. The hybridisation of the nucleic acid probe with the target nucleic acid sequence may be detected by detecting the electrical charge or change in electrical charge intensity from the redox-active tag and/or from the reference probe.

The electrical current may be continuously detected using techniques well known in the art. These include, but are not limited to, electronic methods, for example voltammetry (e.g. cyclic voltammetry) or amperommetry, or optical methods, for example fluorescence or phosphoresence.

Cyclic voltammetry (CV) can carried out on 0.02 $cm^2$ polycrystalline gold electrodes using a Bioanalytical Systems (BAS) Model CV-50W electrochemical analyzer at 20±2 degrees C. in 100 mM phosphate buffer (pH 7). A normal three-electrode configuration consisting of a modified gold-disk working electrode, a saturated calomel reference electrode (SCE, Fisher Scientific), and a platinum wire auxiliary electrode was used. The working compartment of the electrochemical cell was separated from the reference compartment by a modified Luggin capillary. Potentials can then be reported versus SCE. Heterogeneous electron-transfer rates can be determined and analyzed by CV (Nahir, 1994; Weber, 1994; Tender, 1994).

DETAILED DESCRIPTION OF THE INVENTION

It will be appreciated that whilst the genetic probe of the invention can be used in the method of the invention, this is not essential. Thus all features described in relation to the genetic probe apply as optional, but not essential, features of the method.

In this regard, it will be noted that the method of the invention requires an oligonucleotide probe. This oligonucleotide probe can be provided by using the oligonucleotide probe as present in the genetic probe of the invention, i.e. with the oligonucleotide probe being anchored to a nanoparticle and with the nanoparticle also having a reference probe anchored thereto.

Genetic Probe

The present invention provides a genetic probe, as well as related compositions. The genetic probe includes a nanoparticle, an oligonucleotide probe anchored to the surface of the nanoparticle, and a reference probe anchored to the surface of the nanoparticle.

The nanoparticle may be metallic or non-metallic or a composite of two or more materials.

The nanoparticle may be a metallic nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

In some embodiments the nanoparticle may be prepared from polymeric materials. Illustrative polymeric materials include, but are not limited to, poly(ethylenimine) (PEI), poly(alkylcyanoacrylates), poly(amidoamine) dendrimers (PAMAM), poly(ε-caprolactone) (PCL), poly(lactic-co-glycolic acid) (PLGA), or polyesters (poly(lactic acid) (PLA).

In some embodiments, the nanoparticle may be further coated with molecules for attachment of functional elements. In some cases, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, graphene, ovalbumin or dextrin or cyclodextrin.

In one embodiment the nanoparticle is formed from a material selected from: metals, metal oxides (e.g. titania), silica, graphene, and quantum dots (e.g. CdTe, CdSe, CdS, InP, InAs, $CuInS_2$, $AgInS_2$, or PbSe/PbS).

In one embodiment the nanoparticle used in the present invention comprises a noble metal.

The noble metal nanoparticle may be formed from any one or more of the elements in Groups 10 and 11 of the periodic table of elements. It may be that the noble metal is selected from palladium, silver, platinum and/or gold.

The noble metal nanoparticle may optionally be a composite nanoparticle. It is contemplated that the composite nanoparticle could comprise a noble metal together with one or more of silica or titania or graphene. For example it could be a composite formed from a noble metal (e.g. gold) and graphene.

In other embodiments the nanoparticle is substantially entirely, or solely, formed from noble metal, e.g. gold.

In some embodiments, the noble metal nanoparticle is formed from gold, silver and/or platinum. In some embodiments the noble metal nanoparticle is formed from platinum and/or gold.

In one embodiment the nanoparticle is a gold nanoparticle. The use of gold nanoparticles in medical studies is well-established, e.g. in in vivo sensing. Gold nanoparticles have good chemical stability in a biological medium and good biocompatibility. The surface of gold nanoparticles can be readily derivatised to aid the attachment of functional structures to the particles.

The nanoparticle may in one embodiment have maximum diameter of from 1 to 500 nanometres or from 1 to 400 nm or from 1 to 300 nm or from 1 to 200 nm. For example the nanoparticle may have a maximum diameter of from 3 to 500 nm, or from 3 to 400 nm, or from 3 to 300 nm, or from 3 to 100 nm; in embodiments it may be from 5 to 400 nm, or from 5 to 300 nm, or from 5 to 200 nm, or from 5 to 100 nm. The nanoparticle may have a maximum diameter of from 3 to 250 nm, or from 5 to 250 nm, or from 10 to 250 nm; in embodiments it may be from 3 to 200 nm, or from 5 to 200 nm, or from 10 to 200 nm.

The nanoparticle may in one embodiment have maximum diameter of from 1 to 150 nanometres. For example the nanoparticle may have a maximum diameter of from 3 to 150 nm, or from 5 to 150 nm, or from 10 to 150 nm; in embodiments it may be from 3 to 100 nm, or from 5 to 100 nm, or from 10 to 100 nm.

In some embodiments the nanoparticle may have a maximum diameter of from 3 to 50 nm, or from 5 to 50 nm, or from 10 to 50 nm, e.g. from 10 to 30 nm.

The skilled person will appreciate that the size of nanoparticles can be determined by transmission electron microscopy (TEM). For example, a JEOL 1200 EX TEM transmission electron microscope can be used to image and size the nanoparticles.

The nanoparticle has an oligonucleotide probe anchored to its surface. The anchoring may in one embodiment be due to the oligonucleotide probe being bonded to the surface of the nanoparticle, e.g. covalently bonded. In one embodiment the bonding is via a sulphur linkage, e.g. a sulphur-gold bond.

The two main routes of chemical modification are to either modify the oligonucleotide with a functional group which can covalently bind to the nanoparticle, or to modify the nanoparticle so it can electrostatically bind to the oligonucleotide.

In general, any appropriate chemistry may be used to anchor the oligonucleotide probe to the surface, for example click-chemistry may be used to anchor the oligonucleotide probe to the nanoparticle surface by reaction of a chemical group on the oligonucleotide probe with an opposing/complementary reactive group on the nanoparticle. The nanoparticle surface and/or the oligonucleotide probe may comprise reactive or charged groups for anchoring the oligonucleotide probe to the nanoparticle surface. The anchoring may be via use of a thiol anchor. In one embodiment a thiol anchor may attach to a thymine base on the oligonucleotide probe. The anchor may comprise a phosphoramidate bond. Alternatively, the anchor may comprise a triazole.

The oligonucleotide probe may be anchored by immobilisation using a carbodiimide crosslinker, such as EDC (also called EDAC; 1-Ethyl-3-(3-dimethylaminopropyl) carbodiimide hydrochloride, or DCC (dicyclohexyl carbodiimide). For example, the oligonucleotide probe may be anchored by immobilisation of using the carbodiimide linker upon a surface modified with stearic acid or octadecylamine. In another embodiment, the oligonucleotide probe may be anchored by immobilisation using a carbodiimide crosslinker, such as EDC, upon a surface modified with primary amino groups or aminoethanethiol. In another embodiment, the oligonucleotide probe may be anchored through attachment of nucleic acid, such as ssDNA, onto a phosphoric acid-terminated surface. The phosphoric acid may comprise MBPA (mercaptobutylphosphoric acid). In another embodiment, the oligonucleotide probe may be anchored through attachment of nucleic acid onto a film of aluminum alkenebisphosphonate on the surface of the substrate. In another embodiment, the oligonucleotide probe may be anchored onto a mercaptosilane coating on the surface via the amino groups of the nucleic acid bases. In another embodiment, the oligonucleotide probe may be anchored using functionalised polypyrrole.

The nucleic acid may be anchored using any one of the covalent cross-linking reactions discussed in Pividori et al. *Biosensors & Bioelectronics* 15; pp. 191-303, 2000.

The oligonucleotide probe may comprise a modified nucleotide, comprising a reactive group to form an anchor. The reactive group for attachment to the surface may be termed an anchor unit. The oligonucleotide probe may comprise a modified thymine for use as an anchor. The anchor may comprise a modified thymine. The modified thymine may comprise a deoxythymidine (dT) modified with an anchor unit. The anchor unit may comprise thiol groups, such as dithiols. The anchor unit may comprise at least two or three dithiols as a surface anchor. The anchor unit may comprise a propagylamidopentanol linker attached to the thymine, such as at the C5 position of the thymine. In one embodiment, the oligonucleotide probe may comprise modified thymine comprising a deoxythymidine (dT) modified with anchor unit comprising three dithiols as a surface anchor and a propagylamidopentanol unit attached to the C5 position of the thymine. The reactive group to form an anchor may comprise biotin for linking with streptavidin, or comprise streptavidin for linking with biotin.

The oligonucleotide probe may be anchored to a modified surface by the use of silane coupling agents to introduce functional groups to the surface (such as thiols, amines, or aldehydes) for linking to a nucleic acid probe modified with an appropriate reactive group, which would form an anchoring bond.

It is known in the art to covalently attach oligonucleotides to nanoparticles through a thiol modification on the strand of DNA, forming a covalent bond, e.g. S—Au. See Sandstrom, P. et al, *Langmuir* 19, 7537-7543 (2003).

The most widely used method for covalently coating particles with thiol modified DNA is the 'salt ageing' method developed by the Mirkin group. See Hurst, S. J. et al, *Anal. Chem.* 78, 8313-8 (2006). The thiolated oligonucleotides are added to the nanoparticles in one addition, before the salt concentration is slowly increased. This increase in salt concentration is done over a period of many hours, as adding too much salt at once causes the citrate stabilised nanoparticles to aggregate. The salt allows maximum coating of the particles as it reduces the repulsion between the negatively charged oligonucleotides, allowing for closer packing on the nanoparticle surface.

Among alternative coating methods, Zhang et al. found that lowering the pH of the solution to 3.0 during the DNA attachment step allowed for rapid coverage of nanoparticles. See Zhang, X. et al, *J. Am. Chem. Soc.* 7266-7269 (2012).

The technique of adding a thiol binding group to the oligonucleotide and subsequent attachment via the thiol group can be used in the present invention to anchor the oligonucleotide probe to the surface of the nanoparticle, e.g. gold nanoparticle.

It is also known in the art to use a thioctic acid binding group. This has been found to be more stable, relative to the single thiol bond, when using gold nanoparticles. A bis-thiolated adduct is formed upon reduction of the disulphide which can bind to gold through both sulphur atoms. See Dougan, J. et al, *Nucleic Acids Res.* 35, 3668-75 (2007).

Thus an activated ester form of thioctic acid can be synthesised, e.g. as described in Stokes, R. J. et al, *Chem. Commun. (Camb).* 2811-2813 (2007). Meanwhile, an amine group can be added to the oligonucleotide backbone (e.g. the 5' end), to provide an amine-terminated oligonucleotide. The activated ester can then be coupled to the amine-terminated oligonucleotide, by formation of an amide linkage, giving a thioctic acid modified oligonucleotide.

This technique of adding a thioctic acid binding group to the oligonucleotide and subsequent attachment via the thioctic acid binding group can be used in the present invention to anchor the oligonucleotide probe to the surface of the nanoparticle, e.g. gold nanoparticle.

This technique is preferred, as the thioctic acid includes a C5 chain that creates distance between the surface of the nanoparticle and the tag that is incorporated in the oligonucleotide backbone.

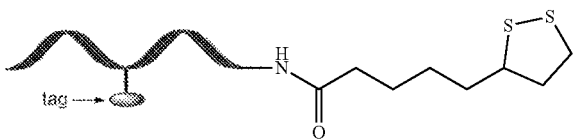

It will be appreciated, however, that the invention is not limited to attachment via a thioctic acid binding group. Any binding group that provides one or more sulphur atom for binding to the metal nanoparticle surface and that includes a chain (such as a C3-18 chain or C5-14 chain or C6-12 chain) which creates distance between the surface of the nanoparticle and the tag that is incorporated in the oligonucleotide backbone, can be beneficial.

In techniques where the oligonucleotide is modified to add a binding group, there will normally be a spacer group between the binding group and the oligonucleotide, sometimes referred to as the spacer region. It is known to vary this spacer group and its size. For example, it is known to use a polyethylene glycol (PEG) spacer group, and it has been found that this increases the loading of oligonucleotides onto the nanoparticle surface, when compared to a spacer group consisting of just 10 A bases or 10 T bases. See Hurst, S. J., et al, *Anal. Chem.* 78, 8313-8 (2006).

In the same reference it has also been described that sonication greatly increased the level of DNA coating on the nanoparticle surface. It was proposed that sonication could reduce the amount of non-specifically bound DNA, exposing more of the nanoparticle surface for the DNA to bind to.

Thus in the present invention it is possible to include a spacer group between the binding group and the oligonucleotide, e.g. a PEG spacer group, to assist with increasing the amount of oligonucleotide probe anchored to the nanoparticle surface.

Alternatively or additionally, in the present invention it is possible to use sonication to assist with increasing the amount of oligonucleotide probe anchored to the nanoparticle surface. For example, sonication for 10 seconds or more, or 15 seconds or more, e.g. from 20 to 60 seconds, may be used.

Another method known in the art for binding oligonucleotides to nanoparticles is to modify the surface of the nanoparticles with a highly cationic compound, such as quaternary ammonium chains. The negatively charged oligonucleotide is then bound to the cationic nanoparticle through electrostatic interactions. This has been used by Sandhu et al. to successfully deliver DNA strands into cells. See Sandhu, K. K. et al, *Bioconjug. Chem.* 13, 3-6 (2002).

This technique of attachment via surface modification of the nanoparticle to make it cationic, e.g. by functionalisation with quaternary ammonium chains, can be used in the present invention to anchor the oligonucleotide probe to the surface of the nanoparticle, e.g. gold nanoparticle.

A benefit of having the oligonucleotide probe anchored to the nanoparticle is that in biological media and upon entering cells, nanoparticle-immobilised DNA strands tend to be more resistant to nucleases that would otherwise quickly degrade the DNA. The genetic probes of the present invention are therefore useful for probing target species (e.g. mRNA) in biological environments.

The oligonucleotide probe comprises an oligonucleotide backbone with a tag incorporated therein via a linker group. Thus in the probe there are nucleotides on either side of the linker group, which is attached to the tag.

Standard phosphoramidite chemistry using automated DNA synthesis can be used to incorporate the linker group (and thus the tag) into the oligonucleotide backbone. Thus the linker group has at least two hydroxy groups, one of which is protected with a DMT (4,4'-dimethoxytrityl) group whilst the other is provided with the reactive phosphoramidite moiety. The automated DNA synthesis can then be carried out on the nucleotide bases plus this linker group.

The oligonucleotide backbone may comprise five or more nucleotides, such as eight or more nucleotides, e.g. from eight to 60 nucleotides, or from nine to 50, or from 10 to 40, or from 12 to 30, or from 15 to 25 nucleotides.

In one embodiment, the oligonucleotide backbone may be at least about 8 nucleotides in length. In another embodiment, the oligonucleotide backbone may be at least about 10 nucleotides in length. In another embodiment, the oligonucleotide backbone may be at least about 12 nucleotides in length. In another embodiment, the oligonucleotide backbone may be at least about 15 nucleotides in length. In another embodiment, the oligonucleotide backbone may be no more than about 15 nucleotides in length.

The oligonucleotide backbone may in one embodiment be no more than about 40 nucleotides in length. In another embodiment, the oligonucleotide backbone may be no more than about 30 nucleotides in length. In another embodiment, the oligonucleotide backbone may be no more than about 20 nucleotides in length. In one embodiment, the oligonucleotide backbone may be between about 8 and about 50 nucleotides in length. In another embodiment, the oligonucleotide backbone may be between about 8 and about 35 nucleotides in length. In another embodiment, the oligonucleotide backbone may be between about 8 and about 30 nucleotides in length. In another embodiment, the oligonucleotide backbone may be between about 10 and about 20 nucleotides in length. In another embodiment, the oligonucleotide backbone may be about 15 nucleotides in length.

The oligonucleotide backbone may comprise or consist of DNA. The oligonucleotide backbone may comprise or consist of RNA. In one embodiment, the oligonucleotide backbone is an oligoribonucleotide. In another embodiment, the oligonucleotide backbone may comprise or consist of a nucleotide analogue or derivative, such as a functional nucleotide analogue or derivative having equivalent complementation as DNA or RNA. The oligonucleotide backbone may comprise combinations of DNA, RNA and/or nucleotide analogues. Nucleotide analogues may comprise PNA or LNA. In another embodiment, the oligonucleotide backbone may comprise or consist of PMO.

The linker group, and thus the tag, may be located at any suitable position within the oligonucleotide backbone.

In one embodiment the linker group is located five or more nucleotides from the end of the oligonucleotide that is anchored to the surface of the nanoparticle, such as seven or more, or nine or more, or 11 or more, or 13 or more, or 15 or more. For example is may be located between seven and 20 nucleotides from the end of the oligonucleotide that is anchored to the surface of the nanoparticle.

This location of five or more nucleotides from the anchored end is preferred, as this creates distance between the surface of the nanoparticle and the tag that is attached to the linker group.

In one embodiment, the oligonucleotide probe comprises or consists of the P21 oligonucleotide probe: 5'-AGTCGCGXCTCAGCT-3' (SEQ ID NO: 1), wherein X is the site of the tag. In another embodiment, the oligonucleotide probe comprises or consists of the BRAF SNP oligonucleotide probe: 5'-AGATTTCXCTGTAGC-3' (SEQ ID NO: 2), wherein X is the site of the tag.

The tag is a fluorescent tag or a redox-active tag. The tag is suitably capable of partial insertion and stacking between adjacent base pairs of double-stranded oligonucleotides.

The tag is therefore suitably a planar aromatic or heteroaromatic moiety or a planar macrocyclic transition metal complex.

The fluorescent tag may be a fluorophore molecule from any of the known organic non-protein fluorophores. Suitably it comprises an aromatic or heteroaromatic structure with three or four rings. In one embodiment there is a fused ring structure; for example there may be two rings fused together or three rings fused together or four rings fused together. There may be a linked pair of fused rings, where each pair has two rings fused together.

The fluorescent tag may be based on any of the following chemical families: thiazine (e.g. methylene blue) or thiazole (e.g. thiazole orange)cyclidene or cyanine (e.g. YOYO-1) or pyrene or xanthene (e.g. fluorescein) or acridine (e.g. acridine orange) or anthracene or anthraquinone.

In one embodiment the fluorescent tag comprises an aromatic or heteroaromatic three ring structure. It may be that the three rings are fused together. For example, it may be selected from: xanthene, anthracene, anthraquinone, and acridine; and derivatives thereof.

In one embodiment the fluorescent tag comprises an aromatic or heteroaromatic four ring structure. In one embodiment, the four rings are fused, e.g. it may be pyrene or derivatives thereof. In one embodiment there are two pairs of fused rings linked together by a bridging non-aromatic moiety (e.g. a C1-4 alkylene or alkenylene group). For example, it may be thiazole orange or oxazole yellow or derivatives thereof.

In one embodiment the derivatives may be substituted versions of the aromatic or heteroaromatic ring structures, where one or more (e.g. one, two, three or four) hydrogen atoms may optionally be substituted with a group independently selected from hydroxyl, carboxyl, C1-4 alkyl, amino (NR'$_2$, where each R' is independently selected from H and C1-4 alkyl), C1-C4 ether, sulfate, thiol, C1-C4 thioether, nitro, nitrile, C1-C4 ester, phenyl, pyridinyl, pyrimidinyl, furanyl, pyrrolyl, thiophenyl, imidazolyl, and thiazolyl. It may be that the derivatives are substituted versions of the fused three ring structures, where one or more (e.g. one, two, three or four) hydrogen atoms are optionally substituted with a group independently selected from hydroxyl, carboxyl, C1-4 alkyl, amino (NR'$_2$, where each R' is independently selected from H and C1-4 alkyl), and C1-C4 ether.

For example, acridine derivatives include proflavin, acridine orange, acridine red, and acridine yellow.

In one embodiment, the fluorescent tag is thiazole orange, pyrene, xanthene, anthracene, anthraquinone, or acridine, or derivatives thereof.

In one embodiment, the fluorescent tag is thiazole orange, pyrene, anthracene, anthraquinone, or acridine, or derivatives thereof.

In one embodiment, the fluorescent tag is thiazole orange, pyrene or anthracene, or derivatives thereof. In one embodiment, the fluorescent tag is thiazole orange, pyrene or anthracene.

In one embodiment, the fluorescent tag is anthracene or derivatives thereof. In one such embodiment, the fluorescent tag is anthracene.

A "redox-active" tag refers to a compound that can be oxidized and reduced, i.e. which contains one or more chemical functions that accept and transfer electrons.

The redox-active tag may be a redox-active molecule from any of the known non-protein redox-active molecules. It may suitably include one or more organic group.

In one embodiment the redox-active tag comprises an aromatic or heteroaromatic structure with three or four rings. In one embodiment there is a fused ring structure; for example there may be a two rings fused together or three rings fused together or four rings fused together. There may be a linked pair of fused rings, where each pair has two rings fused together.

The redox-active tag may be based on any of the following chemical families: phenanthridines (e.g. ethidium), phenothiazines (e.g. methylene blue), phenazines (e.g. phenazine methosulfate), acridines (e.g. quinacrine), anthraquinones (e.g. daunomycin). The redox-active tag may be based on metal complexes containing intercalating ligands (e.g. chrysene, dipyridophenazine, phi). The redox-active tag may be based on a planar macrocyclic transition metal complex (e.g. Ni(II) or Cu(II) [14] cyclidene).

In one embodiment the redox-active tag comprises a macrocyclic transition metal complex. The skilled person will appreciate that a macrocyclic transition metal complex comprises a cyclic ligand compound having a ring size of at least nine and having three or more donor sites, with a transition metal bonded in its centre. A four-coordinate macrocyclic transition metal complex has four donor sites.

In one embodiment the redox-active tag is selected from four-coordinate macrocyclic transition metal complexes where the cyclic ligand compound is planar and has a ring size of 10 or more.

In one embodiment the metal for the macrocyclic transition metal complex is cobalt Co (II), nickel Ni(II), copper Cu (II) or iron Fe (II), e.g. Ni(II) or Cu(II).

In one embodiment the cyclic ligand compound is planar and has a ring size of 12 or more, e.g. from 12 to 16. In one embodiment the cyclic ligand compound is planar and has a ring size of 14.

The ring may suitably include one or more double bond, e.g. two or more double bonds, or three or more double bonds, or four or more double bonds. The double bonds may be C=C or C=N.

The ring may suitably include N and/or O donor atoms. In one embodiment one or more of the donor sites is N, such as two or more or three or more. Preferably all four donor sites are N.

The ring is attached to a linker group, which may be of formula (I) set out below.

The ring may optionally also have one or more pendant groups. The pendant groups may substitute one or more hydrogen on any one or more of the carbons in the ring. The pendant groups may, for example, be selected from hydroxyl, carboxyl, C1-4 alkyl, amino (NR'$_2$, where each R' is independently selected from H and C1-4 alkyl), C1-C4 ether, sulfate, thiol, C1-C4 thioether, nitro, nitrile, C1-C4 ester, phenyl, pyridinyl, pyrimidinyl, furanyl, pyrrolyl, thiophenyl, imidazolyl, and thiazolyl.

In one embodiment the one or more pendant groups are selected from hydroxyl, carboxyl, C1-4 alkyl, amino (NR'$_2$, where each R' is independently selected from H and C1-4 alkyl), C1-C4 ether, and C1-C4 ester.

It may that the redox-active tag is a transition metal complex with a cyclidene [14] ligand as shown below:

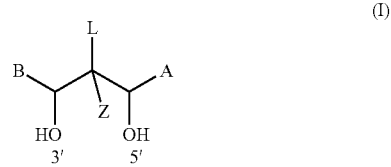

M may, for example, be Ni(II) or Cu(II) or Fe(II) or Co(II). In one embodiment it is Ni(II) or Cu(II).

There may optionally be one or more pendant groups extending off the ring of this cyclidene [14] ligand. These may be as defined above.

It will be appreciated that a four-coordinate macrocyclic transition metal complex can provide the planar configuration that is required for intercalation. Further, cyclidene can be understood to be similar in size and shape to an aromatic fused ring structure such as pyrene. Therefore it can intercalate in a similar manner.

In one embodiment, the redox-active tag is a transition metal complex with a cyclidene [14] ligand as shown below:

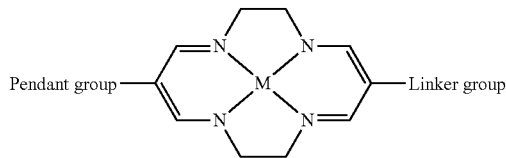

M may, for example, be Ni(II) or Cu(II) or Fe(II) or Co(II). In one embodiment it is Ni(II) or Cu(II).

The linker group suitably provides a three carbon linkage between the nucleotides of the oligonucleotide backbone. This then mimics the spacing that would be provided by a sugar base.

In one embodiment, the linker group may be based on an amino alcohol, such as D- or L-threoninol or serinol.

In one embodiment the linker group is based on D- or L-threoninol. The presence of the stereogenic centre in threoninol allows the selection of one of the two stereoisomers to "tune" the properties of the probe, because this changing of stereochemistry affects how the tag, such as the fluorophore molecule (e.g. anthracene) reacts to different SNP targets.

The linker group may be of formula (I):

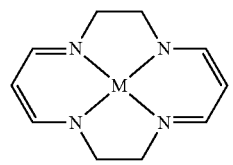

(I)

wherein
L is connected to the tag and is selected from C3-16 alkyl (e.g. C3-14 or C3-12 or C3-10 alkyl), C3-16 alkenyl (e.g. C3-14 or C3-12 or C3-10 alkenyl), and C3-16 alkynyl (e.g. C3-14 or C3-12 or C3-10 alkynyl),
wherein one, two or three carbon atoms may optionally be substituted with a heteroatom independently selected from O, S and N,
and wherein one, two, three or four hydrogen atoms may optionally be substituted with a group independently selected from hydroxyl, carboxyl, amino (NR'$_2$, where each R' is independently selected from H and C1-4 alkyl), C1-C4 alkoxy, C1-C4 ether, C1-C4 thioether, nitro, nitrile, C1-C4 ester, phenyl, pyridinyl, pyrimidinyl, furanyl, pyrrolyl, thiophenyl, imidazolyl, and thiazolyl;
A, B and Z are each independently selected from hydrogen, C1-4 alkyl, amino (NR'$_2$, where each R' is independently selected from H and C1-4 alkyl), and C1-4 alkoxy.

It will be appreciated by the skilled reader that where one, two or three carbon atoms are substituted with a heteroatom independently selected from O, S and N, the number of carbons in the alkyl, cycloalkyl, alkenyl, or alkynyl group is reduced accordingly. Thus in an R group that includes heteroatomic substitution, the number of carbon atoms is given with reference to the hydrocarbon group prior to the heteroatomic substitution; e.g. methylthioethane and methoxyethane are each a C4 alkyl group that has undergone heteroatomic substitution.

The linker group therefore provides a three-carbon spacing between the 3' and 5' hydroxyl groups, which is advantageous due to providing a mimic of a natural sugar spacing. Further, the linker group provides a 5- to 18-carbon spacing between the oligonucleotide and the tag, ensuring that there is sufficient distance between the metal nanoparticle surface and the tag, e.g. the organic fluorophore tag.

In one embodiment L is directly connected to the tag. It may be that L is directly connected to an aromatic ring in the tag, e.g. fluorophore tag.

It may be that L is selected from C3-16 alkyl (e.g. C3-14 or C3-12 or C3-10 alkyl), wherein one, two or three carbon atoms may optionally be substituted with a heteroatom independently selected from O, S and N, and wherein one, two, three or four hydrogen atoms may optionally be substituted with a group independently selected from hydroxyl, carboxyl, amino ($NR'_2$, where each R' is independently selected from H and C1-4 alkyl), C1-C4 alkoxy, C1-C4 ether, and C1-C4 thioether.

It may be that L is selected from C3-16 alkyl (e.g. C3-14 or C3-12 or C3-10 alkyl or C3-6 alkyl), wherein one to three carbon atoms are substituted with a heteroatom independently selected from O, S and N, and wherein one to four hydrogen atoms are substituted with a group independently selected from hydroxyl, carboxyl, amino ($NR'_2$, where each R' is independently selected from H and C1-4 alkyl), C1-C4 alkoxy, C1-C4 ether, and C1-C4 thioether.

In one embodiment the alkyl group is straight chain. However, where the alkyl group has three or more carbon atoms, it may optionally be branched. If the alkyl group is branched, preferably the branch is C1 or C2 and the remainder of the carbon atoms form the backbone of the alkyl group. In particular, embodiments where there is a C1 or C2 sized branch extending from a C2-10 (e.g. C3-10 or C4-10) backbone are envisaged.

In one embodiment the L group contains an ester moiety. Thus a carbon atom is substituted with an O atom and a hydrogen atom is substituted with a carboxyl (=O) group. In one such embodiment the carbon of the ester moiety is directly attached to the tag.

In one embodiment the L group contains an amide moiety. Thus a carbon atom is substituted with an N atom and a hydrogen atom is substituted with a carboxyl group. In one such embodiment the nitrogen of the amide moiety is directly attached to the three-carbon linkage between the 3' and 5' hydroxyl groups.

In one embodiment A, B and Z are each independently selected from hydrogen and C1-4 alkyl and $NH_2$. In one embodiment one or more of A, B and Z is hydrogen. In one embodiment two or more of A, B and Z are each hydrogen.

In one embodiment, one or two of A, B and Z are each hydrogen and one or two of A, B and Z are each C1-3 alkyl, e.g. C1-2 alkyl.

In one embodiment, Z is C1-3 alkyl, e.g. C1-2 alkyl.

In one embodiment the L group is a C3-10 (e.g. C3-6) alkyl where one carbon atom is substituted with O and one hydrogen atom is substituted with carboxyl, so as to provide an ester moiety, where optionally the carbon of the ester moiety is directly attached to the tag, and where Z is C1-3 alkyl, e.g. C1-2 alkyl, and where optionally A and B are both hydrogen.

In one embodiment, Z is hydrogen. In this embodiment the linker group is therefore of formula (Ia):

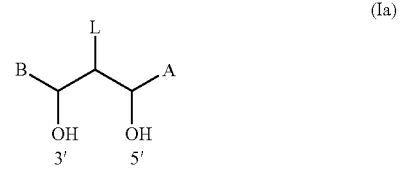

(Ia)

In one embodiment:
L is connected to the fluorophore tag and is selected from C4-16 alkyl (e.g. C4-14 or C4-12 or C4-10 alkyl), C4-16 alkenyl (e.g. C4-14 or C4-12 or C4-10 alkenyl), and C4-16 alkynyl (e.g. C4-14 or C4-12 or C4-10 alkynyl),
wherein one, two or three carbon atoms may optionally be substituted with a heteroatom independently selected from O, S and N,
and wherein one, two, three or four hydrogen atoms may optionally be substituted with a group independently selected from hydroxyl, carboxyl, amino ($NR'_2$, where each R' is independently selected from H and C1-4 alkyl), C1-C4 alkoxy, C1-C4 ether, C1-C4 thioether, nitro, nitrile, C1-C4 ester, phenyl, pyridinyl, pyrimidinyl, furanyl, pyrrolyl, thiophenyl, imidazolyl, and thiazolyl; and
A and B are each independently selected from hydrogen, C1-4 alkyl, amino ($NR'_2$, where each R' is independently selected from H and C1-4 alkyl), C1-4 alkoxy.

This linker group is beneficial in that it provides a 6- to 18-carbon spacing between the oligonucleotide and the tag, ensuring that there is sufficient distance between the metal nanoparticle surface and the tag, e.g. the organic fluorophore tag.

It may be that L is selected from C4-16 alkyl (e.g. C4-14 or C4-12 or C4-10 alkyl), wherein one, two or three carbon atoms may optionally be substituted with a heteroatom independently selected from O, S and N, and wherein one, two, three or four hydrogen atoms may optionally be substituted with a group independently selected from hydroxyl, carboxyl, amino ($NR'_2$, where each R' is independently selected from H and C1-4 alkyl), C1-C4 alkoxy, C1-C4 ether, and C1-C4 thioether.

It may be that L is selected from C4-12 alkyl (e.g. C4-10 alkyl), wherein one to three carbon atoms are substituted with a heteroatom independently selected from O, S and N, and wherein one to four hydrogen atoms are substituted with a group independently selected from hydroxyl, carboxyl, amino ($NR'_2$, where each R' is independently selected from H and C1-4 alkyl), C1-C4 alkoxy, C1-C4 ether, and C1-C4 thioether.

In one embodiment the L group contains an ether moiety. Thus a carbon atom is substituted with an O atom. In one such embodiment the oxygen of the ether moiety is directly attached to the tag, e.g. fluorophore tag. It may be that the oxygen is directly attached to an aromatic ring in the tag, e.g. fluorophore tag.

In one embodiment the L group contains an amide moiety. Thus a carbon atom is substituted with an N atom and a hydrogen atom is substituted with a carboxyl group. In one such embodiment the nitrogen of the amide moiety is directly attached to the three-carbon linkage between the 3' and 5' hydroxyl groups.

In one embodiment the L group is a C4-12 (e.g. C4-10) alkyl group whereby a carbon atom is substituted with an N atom and a hydrogen atom is substituted with a carboxyl group, so as to provide an amide moiety, and a carbon atom is substituted with an O atom, so as to provide an ether moiety. In one such embodiment the oxygen of the ether moiety is directly attached the fluorophore tag, e.g. to an aromatic ring in the fluorophore tag. In one such embodiment the nitrogen of the amide moiety is directly attached to the three-carbon linkage between the 3' and 5' hydroxyl groups.

Further substitutions of carbon and/or hydrogen atoms in accordance with the above definition are permitted.

In one embodiment L is a linker chain that is bonded to the fluorescent tag and is selected from C4-12 alkyl, e.g. C4-10 alkyl, and contains (i) an amide moiety and (ii) an ether moiety. The nitrogen of the amide moiety is suitably directly bonded to the three carbon linkage between the 3' and 5' hydroxyl groups. The oxygen of the ether moiety is suitably directly attached to an aromatic ring of the fluorescent tag. In one embodiment, a C1-8, e.g. C1-7, alkyl chain extends between the ether moiety and the amide moiety. In one embodiment the alkyl group is straight chain. One, two, or three hydrogen atoms may optionally be substituted with a group independently selected from hydroxyl, carboxyl, thiol, and amino ($NR'_2$, where each R' is independently selected from H and C1-4 alkyl); however in one embodiment there are no substituents on the chain.

In one embodiment the L group is —O—(C1-C9 alkyl)-CONH—, such as O—(C1-C8 alkyl)-CONH— or —O—(C1-C7 alkyl-CONH—. In each case one to three hydrogen atoms on the chain may optionally be substituted with a group independently selected from hydroxyl, carboxyl, amino ($NR'_2$, where each R' is independently selected from H and C1-4 alkyl), C1-C4 alkoxy, C1-C4 ether, and C1-C4 thioether.

In one embodiment the alkyl group is straight chain. However, where the alkyl group has three or more carbon atoms, it may optionally be branched. If the alkyl group is branched, preferably the branch is C1 or C2 and the remainder of the carbon atoms form the backbone of the alkyl group. In particular, embodiments where there is a C1 or C2 sized branch extending from a C2-10 (e.g. C3-10 or C4-10) backbone are envisaged.

In one embodiment A and B are each independently selected from hydrogen, C1-4 alkyl and $NH_2$. In one embodiment A and B are each independently selected from hydrogen, C1-3 alkyl and $NH_2$. In one embodiment A and B are each independently selected from hydrogen, C1-2 alkyl and $NH_2$.

In one embodiment A is selected from hydrogen, C1-3 alkyl and $NH_2$ and B is hydrogen.

In one embodiment A and B are both hydrogen, and thus the linker group is based on serinol.

In one embodiment A is methyl and B is hydrogen, and thus the linker group is based on threoninol.

In general, embodiments where A and B are different can be advantageous because there are then stereogenic centres, and changing between the stereoisomers can affect how the tag, e.g. fluorescent tag, reacts to different SNP targets. This therefore allows tuning of the probe.

In one embodiment the linker group is of formula (Ib)

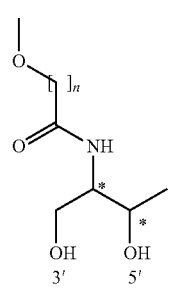

(Ib)

where n is an integer from 1 to 7, e.g. 1, 3, 4, 5, 6 or 7.

The amount of oligonucleotide probe coating the nanoparticle surface can be established by titrating in known amounts of target until no further change in fluorophore tag emission was observed.

In one embodiment there are three or more strands of oligonucleotide probe per nanoparticle, such as four or more or five or more. It may be that there are from three to 5000 strands of oligonucleotide probe per nanoparticle or more, such as from four to 4000 or from five to 3000 or from 10 to 1000, e.g. from 10 to 500 or from 50 to 500.

In one embodiment there are three or more strands of reference probe per nanoparticle, such as four or more or five or more. It may be that there are from three to 5000 strands of reference probe per nanoparticle or more, such as from four to 4000 or from five to 3000 or from 10 to 1000, e.g. from 10 to 500 or from 50 to 500.

In some embodiments the "loading" may be higher. This will of course be to some extent dependent on the size of the particle. For particles smaller than 30 nm, the loading may in some embodiments be 50 or more per nanoparticle, or 100 or more, or 500 or more, or 1000 or more. For particles larger than 30 nm the loading may in some embodiments be 2000 or more per nanoparticle, or 4000 or more, or 6000 or more, or 8000 or more.

In one embodiment the ratio of loading of the oligonucleotide probe to reference probe is about 10:1 to 1:10, e.g. from 5:1 to 1:5 or from 3:1 to 1:3, or from 2:1 to 1:2. It may be that the loading ratio is about 1:1. It may be that there is up to ten times more reference probe than oligonucleotide probe, e.g. up to 5 times as much or up to 4 times as much or up to two times as much reference probe than oligonucleotide probe per nanoparticle. It may be that there is up to ten times more oligonucleotide probe than reference probe, e.g. up to 5 times as much or up to 4 times as much or up to two times as much oligonucleotide probe than reference probe per nanoparticle.

The surface density of the oligonucleotide probe on the metal nanoparticle may be $1 \times 10^{10}$ per $cm^2$ or more, or $1 \times 10^{11}$ per $cm^2$ or more, e.g. $1 \times 10^{12}$ per $cm^2$ or more, such as from 1 to $5 \times 10^{13}$ per $cm^2$.

The surface density of the reference probe on the metal nanoparticle may be $1 \times 10^{10}$ per $cm^2$ or more, or $1 \times 10^{11}$ per $cm^2$ or more, e.g. $1 \times 10^{12}$ per $cm^2$ or more, such as from 1 to $5 \times 10^{13}$ per $cm^2$.

The genetic probe of the present invention includes a reference probe anchored to the surface of the nanoparticle, wherein the reference probe comprises a marker which is a transition metal-based fluorescent marker or a transition metal-based redox-active marker.

A key benefit of the present invention is the ability to provide successful and accurate ratiometric sensing using a stable probe.

Ratiometric sensing consists of analysing the sensing signal from two separate agents, e.g. two separate fluorophores at two distinct wavelengths or two different redox-active materials. Dividing one signal intensity by another obviates the need to determine the initial probe concentration; this both simplifies and facilitates the sensing process, in particular for analysis in cellular environments where probe concentrations would be difficult to determine. Although ratiometric sensing is not new per se, previous attempts have been limited in their success due to the probe product being unstable or the two separate fluorophores interfering with one another.

In the present invention, the use of a nanoparticle, e.g. a noble metal nanoparticle, provides a successful scaffold on which the two separate fluorophores or redox-active materials can be stably mounted and where these separate fluorophores or redox-active materials do not adversely interfere with one another, nor does the scaffold adversely interfere with either fluorophore/redox-active material.

The anchoring of the reference probe may be due to the reference probe being bonded to the surface of the nanoparticle, e.g. covalently bonded. In one embodiment the bonding is via a sulphur linkage, e.g. a sulphur-gold bond.

This may be via a tethering group that is attached to the marker. In other words, in order for the reference probe to be anchored to the surface of the nanoparticle, e.g. noble metal nanoparticle, a tethering group can be provided that can bind the marker to the surface of the nanoparticle. The tethering group may in particular include one or more terminal sulphur atom.

The marker is in one embodiment a transition metal-based fluorescent marker and in this case it may be a complex of a transition metal with an aromatic ligand or a chelating carboxylate-based ligand.

The transition metal may, for example, be selected from d-block transition metals such as ruthenium, rhodium, tungsten, rhenium, osmium, iridium, platinum, copper and zinc, or from f-block lanthanide metals, such as europium. In one embodiment it is selected from ruthenium, rhodium, iridium, osmium, and zinc. It may, for example, be ruthenium, iridium or osmium. In one embodiment it is ruthenium.

It will be understood that photoluminescence is commonly encountered in transition metal complexes with ligands having low lying Π* orbitals, such as aromatic ligands. In the present invention the ligand is suitably aromatic and preferably heteroaromatic. In some embodiments, the metal complex comprises one or more ligand that includes two or more amine groups. It may be a diamine ligand, such as bipyridine or phenanthroline, or it may be a triamine ligand, such as terpyridine. It may be that the metal complex comprises one, two or three ligands independently selected from bipyridines and phenanthrolines and terpyridines. In some embodiments, the metal complex comprises three ligands independently selected from bipyridines and phenanthrolines and terpyridines. The use of diamine ligands, such as bipyridine or phenanthroline, and triamine ligands, such as terpyridine, is particularly suitable when the metal is a d-block transition metal such as ruthenium, rhodium, iridium or osmium.

However, the ligand may alternatively be a chelating carboxylate-based ligand such as an aminopolycarboxylic acid, e.g. EDTA or NTA or DTPA. This is particularly suitable when the metal is a lanthanide metal, such as europium.

The ligand or ligands in the metal complex may each independently be functionalised or unfunctionalised.

In one embodiment at least one ligand in the marker, e.g. in the metal complex, is functionalised with a tethering group. In one embodiment the tethering group comprises one or more group that provides a terminal sulphur atom, such as a thiol group, thiolane group or dithiolane group. Such a sulphur-containing group allows the complex to bind to the surface of the metal nanoparticle.

Thus in one embodiment the metal complex comprises one or more ligands, e.g. three ligands, independently selected from bipyridines and phenanthrolines and terpyridines, and one or more of these bipyridines and/or phenanthrolines and/or and terpyridines is functionalised with a tethering group comprising one or more sulphur-containing group, such as a thiol group, thiolane group or dithiolane group.

One or more further functional groups may optionally be added to the aromatic rings of the bipyridine and/or phenanthroline and/or and terpyridine ligands. These may be in accordance with the definitions for R given below.

In one embodiment, the metal complex comprises one, two or three ligands (e.g. three ligands) independently selected from ligands of formula (II) and formula (III):

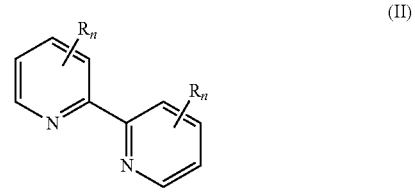

(II)

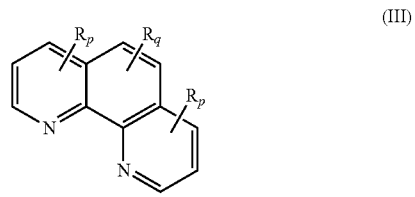

(III)

wherein:
each n is independently selected from 0, 1, 2, 3, or 4;
each p is independently selected from 0, 1, 2, or 3;
the or each q is independently selected from 0, 1, or 2; and
each R is independently selected from C1-18 alkyl (e.g. C2-16 or C3-14 or C4-12 alkyl), C6-18 cycloalkyl (e.g. C6-16 or C6-14 or C6-12 cycloalkyl), C2-C18 alkenyl (e.g. C2-16 or C3-14 or C4-12 alkenyl), and C2-C18 alkynyl (e.g. C2-16 or C3-14 or C4-12 alkynyl),
wherein one, two or three carbon atoms may optionally be substituted with a heteroatom independently selected from O, S and N,
and wherein one, two or three hydrogen atoms may optionally be substituted with a group independently selected from hydroxyl, carboxyl, thiol, thiolane, dithiolane, amino (NR'$_2$, where each R' is independently selected from H and C1-4 alkyl), C1-C4 alkyoxy, C1-C4 ether, C1-C4 thioether, nitro, nitrile, C1-C4 ester, phenyl, pyridinyl, pyrimidinyl, furanyl, pyrrolyl, thiophenyl, imidazolyl, and thiazolyl;
provided that the complex comprises one or more ligand having a terminal sulphur group.

It will be appreciated by the skilled reader that where one, two or three carbon atoms are substituted with a heteroatom independently selected from O, S and N, the number of carbons in the alkyl, cycloalkyl, alkenyl, or alkynyl group is reduced accordingly. Thus in an R group that includes heteroatomic substitution, the number of carbon atoms is given with reference to the hydrocarbon group prior to the heteroatomic substitution; e.g. pyridine is a C6 cycloalkyl group that has undergone heteroatomic substitution.

In one embodiment, each R is independently selected from C1-18 alkyl (e.g. C2-16 or C3-14 or C4-12 alkyl), C6-18 cycloalkyl (e.g. C6-16 or C6-14 or C6-12 cycloalkyl), C2-C18 alkenyl (e.g. C2-16 or C3-14 or C4-12 alkenyl), and C2-C18 alkynyl (e.g. C2-16 or C3-14 or C4-12 alkynyl),
wherein one, two or three carbon atoms may optionally be substituted with a heteroatom independently selected from O, S and N, and wherein one, two or three hydrogen atoms may optionally be substituted with a group independently selected from hydroxyl, carboxyl, thiol, thiolane, dithiolane, amino (NR'$_2$, where each R' is independently selected from H and C1-4 alkyl), C1-C4 alkyoxy, C1-C4 ether, C1-C4 thioether, nitro, nitrile, and C1-C4 ester.

In one embodiment, each R is independently selected from C1-18 alkyl (e.g. C2-16 or C3-14 or C4-12 alkyl), C6-18 cycloalkyl (e.g. C6-16 or C6-14 or C6-12 cycloalkyl), C2-C18 alkenyl (e.g. C2-16 or C3-14 or C4-12 alkenyl), and C2-C18 alkynyl (e.g. C2-16 or C3-14 or C4-12 alkynyl),
  wherein one, two or three carbon atoms may optionally be substituted with a heteroatom independently selected from O, S and N,
  and wherein one, two or three hydrogen atoms may optionally be substituted with a group independently selected from hydroxyl, carboxyl, thiol, thiolane, dithiolane, and amino (NR'$_2$, where each R' is independently selected from H and C1-4 alkyl).

In one embodiment one or more R group contains an amide moiety. Thus a carbon atom is substituted with an N atom and a hydrogen atom is substituted with a carboxyl group.

In one embodiment one or more R group contains an ether moiety. Thus a carbon atom is substituted with an O atom. In one such embodiment the oxygen of the ether moiety is directly attached to an aromatic ring of the ligand.

In one embodiment one or more R group is present which is a C4-16 alkyl group whereby a carbon atom is substituted with an O atom, so as to provide an ether moiety. In one such embodiment the oxygen of the ether moiety is directly attached to an aromatic ring of the ligand.

In one embodiment one or more R group is present which is a C4-16 alkyl group whereby a carbon atom is substituted with an N atom and a hydrogen atom is substituted with a carboxyl group, so as to provide an amide moiety, and a carbon atom is substituted with an O atom, so as to provide an ether moiety. In one such embodiment the oxygen of the ether moiety is directly attached to an aromatic ring of the ligand.

In one embodiment the alkyl group is straight chain. However, the alkyl group may optionally be branched. If the alkyl group is branched, preferably the branch is C1 or C2 and the remainder of the carbon atoms (and any heteroatoms substituted for carbon atoms) form the backbone of the alkyl group.

In some embodiments, the complex comprises one or more ligand having at least two terminal sulphur groups. It may be that the complex comprises one or more ligand having one or more terminal dithiolane group, e.g. one or more terminal 1,2 dithiolane group.

In some embodiments, the complex comprises only one ligand having one or more terminal sulphur group. It may be that said ligand has one or more terminal thiol group. In one embodiment, said ligand has two or more terminal sulphur groups. It may be that said ligand has one or more terminal dithiolane group, e.g. one or more terminal 1,2 dithiolane group.

In one embodiment, the complex includes a ligand of formula (II) where both aromatic rings are provided with an R group that has one or more terminal sulphur group, e.g. two or more terminal sulphur groups, such as one or more terminal 1,2 dithiolane group, or one or more thiol group.

In one embodiment, the complex includes a ligand of formula (III) where two or more of the aromatic rings are each provided with an R group that has a one or more terminal sulphur group, e.g. two or more terminal sulphur groups, such as one or more terminal 1,2 dithiolane group, or one or more thiol group.

In one embodiment, the complex includes a ligand of formula (III) where both outer aromatic rings are provided with an R group that has a one or more terminal sulphur group, e.g. two or more terminal sulphur groups, e.g. one or more terminal 1,2 dithiolane group. Optionally the central aromatic ring is also provided with an R group that has a one or more terminal sulphur group, e.g. two or more terminal sulphur groups, such as one or more terminal 1,2 dithiolane group or one or more thiol group.

In one embodiment, the metal complex comprises three ligands independently selected from ligands of formula (II) and formula (III), and one of said ligands is substituted and the other two are unsubstituted. The substituted ligand has one or more terminal sulphur group, e.g. two or more terminal sulphur groups, e.g. one or more terminal 1,2 dithiolane group or one or more thiol group. It may be that the substituted ligand is a ligand of formula (II) where both aromatic rings are provided with an R group that has one or more terminal thiol groups. It may be that the substituted ligand is a ligand of formula (II) where both aromatic rings are provided with an R group that has two or more terminal sulphur groups, such as one or more terminal 1,2 dithiolane group.

In one embodiment, the metal complex is

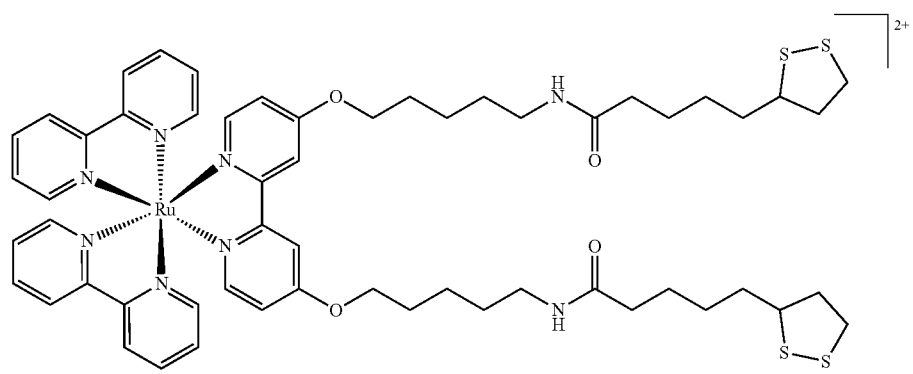

RubpySS

This RubpySS probe is advantageous for use due to its photostability, excitation and emission profiles within the visible region (which are more compatible with conventional imaging techniques) and large Stokes shifts.

The RubpySS probe excitation bands (465 nm, MLCT band) and emission bands (550-800 nm) are distinct from those for anthracene ($\lambda_{ex}$=350 nm, $\lambda_{em}$=370-570 nm). Therefore it is advantageous for use in combination with a fluorescence tag which is anthracene or a derivative thereof.

The presence of the two disulphide terminating legs on the ruthenium probe allow it to bind to the surface of metal nanoparticles, e.g. gold nanoparticles.

Iridium or osmium versions of this complex can also be contemplated.

In one embodiment, the metal complex is:

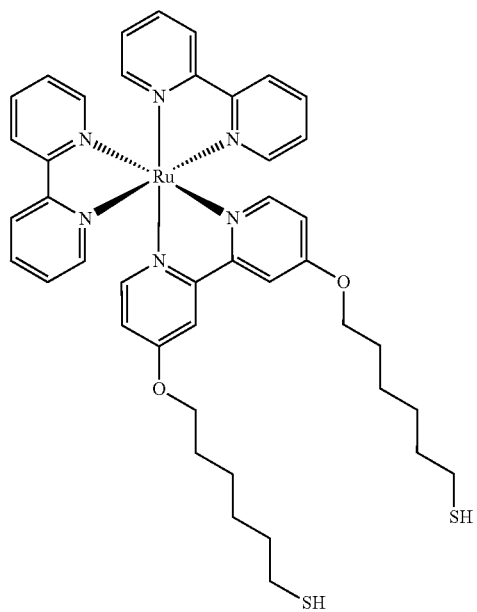

In general, in the genetic probe of the invention it is desired that the fluorescent marker has an excitation band that is not identical to the excitation band of the fluorescent tag. Likewise, it is desired that the fluorescent marker has an emission band that is not identical to the emission band of the fluorescent tag.

In one embodiment the fluorescent tag is based on anthracene and the fluorescent marker is based on a ruthenium bipyridine complex, such as RubpySS.

The marker is in one embodiment a transition metal-based redox-active marker and in this case it may be a complex of a transition metal with an aromatic ligand.

This may be a complex of the type described above for the transition metal-based fluorescent marker. For example, the transition metal-based redox-active marker may be a metal complex that comprises one or more ligands, e.g. three ligands, independently selected from bipyridines and phenanthrolines and terpyridines, where one or more of these bipyridines and/or phenanthrolines and/or and terpyridines is functionalised with a tethering group comprising one or more sulphur-containing group, such as a thiol group, thiolane group or dithiolane group, and where the metal is a d-block transition metal such as ruthenium, rhodium, iridium or osmium. The ligands may be of formula (II) or (III) as defined above.

In particular, the transition metal-based redox-active marker may be RubpySS.

However, other transition metal-based redox-active markers can also be contemplated. Examples include, but are not limited to, any neutral or negatively charged probes, for example ferricyanide/ferrocyanide, ferrocene and derivatives thereof (e.g., dimethylaminomethyl-, monocarboxylic acid-, or dicarboxylic acid-derivatives of ferrocene), hexacyanoruthenate, and hexacyanoosmate.

In one embodiment transition metal-based redox-active marker is functionalised with a tethering group. In one embodiment the tethering group comprises one or more group that provides a terminal sulphur atom, such as a thiol group, thiolane group or dithiolane group. Such a sulphur-containing group allows the complex to bind to the surface of the metal nanoparticle.

It will be appreciated that the transition metal-based redox-active marker is chosen so that it has a different redox potential to the redox-active tag.

In one embodiment the redox-active tag is a transition metal complex based on a cyclidene [14] ligand, and the redox-active marker is based on a ruthenium bipyridine complex, such as RubpySS, or ferrocene.

The genetic probe may be prepared by combining techniques and methods known in the art. Obtaining or preparing noble metal nanoparticles is known and is illustrated in the examples. Obtaining or preparing an oligonucleotide is known and is illustrated in the examples. Obtaining or preparing an organic fluorescent tag (e.g. anthracene) is known and the attachment of a linker group can be achieved via known synthetic chemistry routes and is illustrated in the examples. The oligonucleotide can be prepared with the organic fluorescent tag incorporated therein via the linker group. The oligonucleotide can be modified to aid attachment to the nanoparticle, e.g. via thioctic acid modification, as is illustrated in the examples. Obtaining or preparing a transition metal-based fluorescent marker is known, as is providing that marker with tether groups, e.g. dithiolane groups (e.g. RubpySS).

The oligonucleotide probe and the reference probe can then be attached to the surface of the nanoparticles. When preparing the genetic probe of the invention, it may be that the oligonucleotide probe is firstly added to the metal nanoparticles, followed by addition of the reference probe. This has been found to be an effective route to synthesis of the genetic probe.

Method of Determining SNPs or Single Nucleotide Modifications

The present invention also provides a method of determining the percentage of single nucleotide polymorphisms (SNPs) or single nucleotide modifications of a target nucleic acid in a pool (population) of the target nucleic acid.

In one embodiment this method makes use of a genetic probe in the form as described above, but this is not essential.

The pool of target nucleic acid may be in a sample. The sample may comprise a cell lysate, a bodily fluid sample, or a nucleic acid sample, such as a sample of purified or partially purified nucleic acid. The target nucleic acid may be eukaryote, prokaryote or viral nucleic acid. The eukaryote nucleic acid may be mammalian or fungal nucleic acid. In one embodiment the target nucleic acid is human. The target nucleic acid may be associated with a disease or condition or a known SNP. The target nucleic acid sequence may comprise or consist of DNA or RNA. The target nucleic acid sequence may comprise a mixture of DNA and RNA. The target nucleic acid sequence may comprise genomic nucleic acid. The target nucleic acid sequence may comprise viral RNA; mRNA; ncRNA; small RNA; and siRNA; or combinations thereof. The target nucleic acid sequence may comprise mitochondrial nucleic acid. The target nucleic acid sequence may comprise or consist of chromosomal and/or non-chromosomal DNA. In one embodiment, the target nucleic acid comprises circulating DNA, such as circulating tumour DNA (ctDNA)

In one embodiment, the target nucleic acid sequence comprises mRNA transcript. In another embodiment, the target nucleic acid sequence may comprise cDNA formed from mRNA transcripts. PCR amplification may be used to increase copy number prior to analysis, for example in the case of cDNA being detected.

In another embodiment, the pool of target nucleic acid may be in situ in a single cell or a population of cells. The cell or population of cells may be eukaryote or prokaryote. The cell or population of cells may be mammalian or fungal. The cell or population of cells may be human. The cell, population of cells, or sample may be derived from a patient. For example, it may be a patient having a condition, or suspected of having a condition, or at risk of having a condition. The cell, population of cells, or sample may be derived from a patient of unknown condition. The target nucleic acid, cell or population of cells may be from a subject who has, or is suspected to have, or is at risk of having, a condition associated with an SNP or single nucleotide modification. The SNP or single nucleotide modification target nucleic acid may be associated with a disease or condition. The SNP or single nucleotide modification target nucleic acid may be indicative of a disease or condition. The indication may be diagnostic or prognostic. The indication may be an indication of risk or likelihood of developing a disease or condition. Such conditions may comprise cancer or Alzheimer's Disease. In another embodiment, the condition may be Sickle Cell Anaemia. The skilled person will recognise that the invention herein would be useful for detecting and monitoring any disease or condition associated with a SNP or single nucleotide modification.

The condition or disease associated with a SNP may comprise cancer, such as breast cancer, lung cancer, colorectal cancer or melanoma. The lung cancer may be associated with a SNP in the genes of PIK3CA, KRAS, NRAS, AKT1, ALK, or EGFR, or combinations thereof. The colorectal cancer may be associated with a SNP in the genes of KRAS and/or PIK3CA. The breast cancer may be associated with a SNP in BRAF.

The condition associated with a SNP may comprise Alzheimer's disease or Sickle Cell Anaemia. The Alzheimer's Disease may be associated with an SNP in the P21 gene.

The SNP may in any of the genes selected from P21, BRAF, PIK3CA, KRAS, NRAS, AKT1, ALK, and EGFR, or combinations thereof.

The cancer may comprise cancer associated with an SNP in the BRAF gene, such as some breast cancers. The Alzheimer's Disease may be associated with an SNP in the P21 gene. The SNP may comprise the P21 gene transversion (rs1801270; C to A); associated with Alzheimer's Disease. The SNP may comprise BRAF gene transversion (V600E; X=T to A), which is associated with cancer.

The target nucleic acid may comprise sequence of the BRAF gene, or P21 gene. In one embodiment, the target nucleic acid comprises the P21 ribonucleic acid target:

3'-UCAGCGCXGAGUCGA-5' (SEQ ID NO: 18), wherein X is the site of the SNP. In another embodiment, the target nucleic acid comprises the P21 deoxyribonucleic acid target: 3'-TCAGCGCXGAGTCGA-5' (SEQ ID NO: 19), wherein X is the site of the SNP. In another embodiment, the target nucleic acid comprises the BRAF SNP nucleic acid target: 3'-TCTAAAGXGACATCG-5' (SEQ ID NO: 20), wherein X is the site of the SNP.

In one embodiment, the SNP comprises a sequence variation of a single nucleotide to an alternative nucleotide. The nucleotide that is subject to a polymorphism may comprise adenine (A), thymine (T), cytosine (C), or guanine (G), or in the case of RNA, adenine (A), uracil (U), cytosine (C), or guanine (G).

In another embodiment, the nucleotide modification comprises or consists of a natural or synthetic modification to a nucleotide. The nucleotide modification may comprise methylation of the nucleic acid. The nucleotide modification may comprise hydroxymethylation of the nucleic acid. In another embodiment, the nucleotide modification comprises or consists of an 8-oxoguanine modification. In one embodiment, the nucleotide of the target nucleic acid to be interrogated by the oligonucleotide probe may comprise a methylated nucleotide, such as a methylated cytosine. In one embodiment, the methylated nucleotide may be hydroxymethylated.

The oligonucleotide probe may comprise or consist of DNA. The oligonucleotide probe may comprise or consist of RNA. In one embodiment, the oligonucleotide probe is an oligoribonucleotide. In another embodiment, the oligonucleotide probe may comprise or consist of a nucleotide analogue or derivative, such as a functional nucleotide analogue or derivative having equivalent complementation as DNA or RNA. The oligonucleotide probe may comprise combinations of DNA, RNA and/or nucleotide analogues. Nucleotide analogues may comprise PNA or LNA. In another embodiment, the oligonucleotide probe may comprise or consist of PMO.

In one embodiment, the oligonucleotide probe may be at least about 8 nucleotides in length. In another embodiment, the oligonucleotide probe may be at least about 10 nucleotides in length. In another embodiment, the oligonucleotide probe may be at least about 12 nucleotides in length. In another embodiment, the oligonucleotide probe may be at least about 15 nucleotides in length. In another embodiment, the oligonucleotide probe may be no more than about 15 nucleotides in length. In another embodiment, the oligonucleotide probe may be no more than about 20 nucleotides in length. In another embodiment, the oligonucleotide probe may be no more than about 30 nucleotides in length. The oligonucleotide probe may be no more than about 40 nucleotides in length. In one embodiment, the oligonucleotide probe may be between about 8 and about 50 nucleotides in length. In another embodiment, the oligonucleotide probe may be between about 8 and about 35 nucleotides in length. In another embodiment, the oligonucleotide probe may be between about 8 and about 30 nucleotides in length. In another embodiment, the oligonucleotide probe may be between about 10 and about 20 nucleotides in length. In another embodiment, the oligonucleotide probe may be about 15 nucleotides in length.

The oligonucleotide probe may comprise a known/predetermined sequence. The oligonucleotide probe may be complementary to the target nucleic acid sequence. The oligonucleotide probe may be 100% complementary to the target nucleic acid sequence, with the exception of the fluorescent tag position. The oligonucleotide probe may be at least about 95%, or at least about 90% complementary to the target nucleic acid sequence. The oligonucleotide probe may be at least about 80% complementary to the target nucleic acid sequence. The oligonucleotide probe may be substantially complementary to the target nucleic acid sequence along the whole length of the oligonucleotide probe, with the exception of the fluorescent tag position. The oligonucleotide probe may be complementary to the target nucleic acid sequence along a length of at least about 8 consecutive nucleotides of the probe. The oligonucleotide probe may be complementary to the target nucleic acid sequence along a length of at least about 10 consecutive nucleotides of the probe. The oligonucleotide probe may be complementary to the target nucleic acid sequence along a length of at least about 15 consecutive nucleotides of the probe. The oligonucleotide probe may be complementary to the target nucleic acid sequence along a length of at least about 18 consecutive nucleotides of the probe. The oligonucleotide probe may be complementary to the target nucleic acid sequence along a length of at least about 25 consecutive nucleotides of the probe. The oligonucleotide probe may be sufficiently complementary to the target nucleic acid sequence to be able to selectively hybridise under stringent conditions. The oligonucleotide probe may hybridise to target nucleic acid, such as under stringent conditions.

In one embodiment, the oligonucleotide probe comprises or consists of the P21 oligonucleotide probe: 5'-AGTCGCGXCTCAGCT-3' (SEQ ID NO: 1), wherein X is the site of the organic fluorescent tag or redox-active tag. In another embodiment, the oligonucleotide probe comprises or consists of the BRAF SNP oligonucleotide probe:

5'-AGATTTCXCTGTAGC-3' (SEQ ID NO: 2), wherein X is the site of the organic fluorescent tag or redox-active tag.

Where reference is made to an oligonucleotide probe sequence, the skilled person will understand that one or more substitutions may be tolerated, optionally two substitutions may be tolerated in the sequence, such that it maintains the ability to hybridize to the target sequence, or where the substitution is in a target sequence, the ability to be recognized as the target sequence. References to sequence identity may be determined by BLAST sequence alignment (ncbi.nlm.nih.gov/BLAST/Y) using standard/default parameters. For example, the sequence may have at least 99% identity and still function according to the invention. In other embodiments, the sequence may have at least 98% identity and still function according to the invention. In another embodiment, the sequence may have at least 95% identity and still function according to the invention.

In the method of the invention the oligonucleotide probe may be anchored to or capable of being anchored to a surface. The oligonucleotide probe may be conjugated to, or bound by, a nanoparticle-based delivery vehicle. A nanoparticle may be a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof. In some embodiments a nanoparticle may be prepared from polymeric materials. Illustrative polymeric materials include, but are not limited to, poly(ethylenimine) (PEI), poly(alkylcyanoacrylates), poly(amidoamine) dendrimers (PAMAM), poly(ε-caprolactone) (PCL), poly(lactic-co-glycolic acid) (PLGA), or polyesters (poly(lactic acid) (PLA). In some embodiments, a nanoparticle may be further coated with molecules for attachment of functional elements. In some cases, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, graphene, ovalbumin or dextrin or cyclodextrin. In some embodiments, a nanoparticle may have at least one dimension of less than about 500 nm, 400 nm, 300 nm, 200 nm, 100 nm, 80 nm, or 50 nm.

In one embodiment, the oligonucleotide probe used in the method is as defined above in relation to the genetic probe product. Therefore it is anchored to a noble metal nanoparticle.

The difference in intensity of the light emission of the fluorescent tag depending on the nucleotide's identity or modified structure may be a detectable increase in intensity or a detectable decrease in intensity. The difference in intensity of the electrical charge of the redox-active tag depending on the nucleotide's identity or modified structure may be a detectable increase in intensity or a detectable decrease in intensity. The skilled person will recognise that the intensity will differ (i.e. increase or decrease) depending on the tag and/or the paired nucleotide, or modification thereof. For example, in an embodiment wherein the organic fluorescent tag is anthracene, the anthracene may provide a detectable increase in intensity when paired with A relative to a pairing with T. The anthracene may provide a detectable decrease in intensity when paired with C relative to a pairing with T.

The difference in the light emission wavelength of the fluorescent marker relative to the light emission wavelength of the fluorescent tag of the oligonucleotide probe may be a difference in the respective peak emissions. The difference in the light emission wavelength of the fluorescent marker relative to the light emission wavelength of the fluorescent tag of the oligonucleotide probe may be at least 50 nm. The difference in the light emission wavelength of the fluorescent marker relative to the light emission wavelength of the fluorescent tag of the oligonucleotide probe may be between about 50 nm and 400 nm, or more. The difference may be about 200 nm.

The calibration may comprise the detection of a percentage change in emission intensity upon hybridization of the oligonucleotide probe to a plurality of standards of target nucleic acid with a known SNP or single nucleotide modification ratio. At least three different ratio standards may be used for calibration.

In one embodiment, comparing the percentage change in emission of the fluorescent tag to a calibration value that has been determined by linear regression of the percentage change in emission of known standards comprises the calculation of the percentage of single nucleotide polymorphisms (SNPs) or single nucleotide modifications in accordance with the linear regression calculation of $Y=a+bX$, where X is the explanatory variable (percentage change in emission) and Y is the dependent variable (the percentage of single nucleotide polymorphisms (SNPs) or single nucleotide modifications). The slope of the line is b, and a is the intercept (the value of y when x=0).

The method may further comprise the use of a second genetic probe. An identical assay may be undertaken with a separate/second genetic probe. The second genetic probe may comprise a different linker length to the tag relative to the first genetic probe. Additionally, or alternatively, the second genetic probe may comprise a different linker stereochemistry and/or a different organic fluorescent tag or redox-active tag relative to the first genetic probe.

The use of a second genetic probe overcomes a problem in some situations, for example if no target is present or the calibration line crosses the x-axis at a particular ratio of one base to another. For example, at the point at which the calibration line crosses the x-axis, it would not be clear in a test with a single genetic probe whether (i) there is no target present in solution or (ii) if the ratio is below the x-axis threshold of the calibration curve. However this could be addressed by a dual genetic probe approach where the intercept with the x-axis would occur at a different base ratio value. A dual genetic probe approach would also give a further verification of the results obtained.

Additionally or alternatively the method may further comprise the use of a second fluorescent tag/reporter or second redox-active tag/reporter on the genetic probe. The second fluorescent tag/reporter or second redox-active tag/reporter may indicate duplex formation through a change in intensity of the emission or electrical charge as appropriate.

Advantageously, the use of a second fluorescent tag/reporter or second redox-active tag/reporter overcomes the problem in some situations, for example if no target is present or the calibration line crosses the x-axis at a particular ratio of one base to another. The second fluorescent tag/reporter or second redox-active tag/reporter can indicate duplex formation, thereby confirming the presence or absence of the target nucleic acid, and the potential need to use an alternative or second genetic probe to read out the ratio that is below the calibration x-axis threshold for the first genetic probe. Further advantageously, a second fluorescent tag/reporter or second redox-active tag/reporter also allows a ratiometric method for reading out the SNP variant ratio. For example, the ratio value between the two probes can provide an adjustment value/factor to be applied in order to account for differences in concentration of the probe.

According to another aspect of the invention, there is provided a method of determining the status of a condition associated with a known SNP in a subject, the method comprising:
  providing a sample from the subject comprising a target nucleic acid, wherein the target nucleic acid may comprise the SNP;
  determining the percentage of the SNP in the sample relative to target nucleic acid not having the SNP in accordance with the method of the invention herein,
  wherein the percentage of the SNP is indicative of the status of the condition associated with the SNP in the subject.

In one embodiment, the status may provide a diagnosis and/or prognosis for the condition. Additionally or alternatively, the status may comprise the progression of the condition. Further additionally or alternatively, the status may comprise the severity of the condition.

The invention can also be used for epigenetic screening purposes (i.e. to establish the Me-C/C ratio within a sample), given that the probes can also discern base modifications (i.e. methylation of cytosine) as well as base changes.

According to another aspect of the invention, there is provided a method of determining the epigenetic status of a target nucleic acid of a subject, the method comprising determining the percentage of single nucleotide modifications of the target nucleic acid in accordance with the method herein,
  wherein the percentage of the single nucleotide modifications of the target nucleic acid is indicative of the epigenetic status of the target nucleic acid in the subject.

In one embodiment, the epigenetic status may comprise the extent of genetic regulation of a target nucleic acid wherein the regulation is associated with the single nucleotide modifications. The epigenetic status may comprise the determination of the extent of methylation or hydroxymethylation of a nucleotide in a target nucleic acid, in particular, a nucleic acid involved in genetic regulation. The methylation/hydroxymethylation may comprise cytosine methylation/hydroxymethylation.

According to another aspect of the invention, there is provided the use of a genetic probe in accordance with the invention herein, for determining the SNP ratio or single nucleotide modification ratio of target nucleic acid in a pool of the target nucleic acid.

The use may be in vitro. In another embodiment the use may be in vivo. In another embodiment the use may be in situ in a cell or population of cells. The population of cells may be a tissue.

According to another aspect of the invention, there is provided the use of a genetic probe in accordance with the invention herein, for diagnosis and/or prognosis of a condition associated with a SNP or single nucleotide modification in a subject.

The condition or disease associated with a SNP may comprise cancer, such as breast cancer, lung cancer, colorectal cancer or melanoma. The lung cancer may be associated with a SNP in the genes of PIK3CA, KRAS, NRAS, AKT1, ALK, or EGFR, or combinations thereof. The colorectal cancer may be associated with a SNP in the genes of KRAS and/or PIK3CA. The breast cancer may be associated with a SNP in BRAF.

The condition associated with a SNP may comprise Alzheimer's disease or Sickle Cell Anaemia. The Alzheimer's Disease may be associated with an SNP in the P21 gene.

The SNP may in any of the genes selected from P21, BRAF, PIK3CA, KRAS, NRAS, AKT1, ALK, and EGFR, or combinations thereof.

The condition associated with a single nucleotide modification may comprise Barrett's oesophagus or cancer, such as colorectal cancer. The colorectal cancer may be associated with MLH1 methylation. The single nucleotide modification may comprise methylation of MLH1.

According to another aspect of the invention, there is provided a kit for the detection and analysis of the ratio of a SNP and/or a single nucleotide modification of a target nucleic acid in a pool of the target nucleic acid, wherein the kit comprises:
  the genetic probe according to the invention herein, or an oligonucleotide probe comprising an oligonucleotide backbone with a tag incorporated therein via a linker group, wherein either the tag is an organic fluorescent tag or a redox-active tag, and wherein the tag is in a position that is arranged to be paired with a nucleotide of the target nucleic acid to be interrogated; and
  a first standard target nucleic acid for use as a standard in a calibration, wherein the first target nucleic acid comprises the SNP or single nucleotide modification to be analysed; and
  a second standard target nucleic acid for use as a standard in calibration, wherein the second target nucleic acid does not comprise the SNP or single nucleotide modification to be analysed.

In one embodiment, the first and second standard target nucleic acids are provided in a standard mixture having a predetermined ratio for use in the calibration. The kit may comprise 1, 2, 3, 4, 5, 6 or more standard mixtures of the first and second standard target nucleic acids in different predetermined ratios. For example, a first standard mixture may comprise 1:0 of the first standard target nucleic acid relative to the second standard target nucleic acid. A second standard mixture may comprise 1:1 of the first standard target nucleic acid relative to the second standard target nucleic acid. A third standard mixture may comprise 0:1 of the first standard target nucleic acid relative to the second standard target nucleic acid. A fourth standard mixture may comprise 2:1 of the first standard target nucleic acid relative to the second standard target nucleic acid. A fifth standard mixture may comprise 1:2 of the first standard target nucleic acid relative to the second standard target nucleic acid. Additionally or alternatively, the kit may further comprise a standard calibration chart, comprising an indication of the change in intensity of the emission or electrical charge relative to the percentage of the SNP or single nucleotide modification in a pool of target nucleic acid. Additionally or alternatively, the kit may comprise a linear regression formula to be used with the recorded change in intensity of the emission or electrical charge in the pool of target nucleic acid.

The kit may comprise an exonuclease, such as a T4 exonuclease to convert dsDNA to single stranded. The kit may further comprise primers and/or a polymerase for amplification, such as LAMP or PCR amplification, of the target nucleic acid. The primers may comprise Loop primers for loop mediated isothermal amplification (LAMP). The kit may further comprise a reverse transcriptase for conversion of RNA sequences to cDNA.

The methods and use of the invention herein may be carried out at room temperature. Room temperature may be about 24° C., for example between about 20-26° C. The methods of the invention herein may be carried out below or substantially below the melting temperature of the oligonucleotide probe and the target nucleic acid, for example at least 5° C. the melting temperature of the oligonucleotide probe and the target nucleic acid. The methods of the invention herein may be carried out below 40° C., 35° C., 32° C., 30° C., or 28° C.

The term "genetic" in the context of genetic probe or genetic sensor described herein is understood to mean a sensor or probe that is capable of analysis or interrogation of a nucleic acid sequence. Such term includes, but is not limited, to gene sequences, intergenic sequence, or any sequence of nucleic acid. Synthetic nucleic acid sequences may also be capable of analysis/interrogation.

The term "condition or disease associated with" used herein is understood to include a disease or condition of a subject that is directly or indirectly caused by the SNP or single nucleotide modification. The SNP or single nucleotide modification may or may not be the single causative modification leading to the condition or disease, for example the SNP or single nucleotide modification may contribute to the condition or disease in association with other contributing factors. The association may be a clinical association. The association may be a statistical association. The detection and/or finding of a particular ratio of a SNP or single nucleotide modification may indicate a higher risk of having or developing the disease or condition in a subject.

Other modifications, symptoms or clinical manifestations may be used to contribute to determining the status, diagnosis or prognosis of the condition or disease.

The skilled person will understand that optional features of one embodiment or aspect of the invention may be applicable, where appropriate, to other embodiments or aspects of the invention.

Embodiments of the invention will now be described in more detail, by way of example only, with reference to the accompanying drawings.

Figure 1:
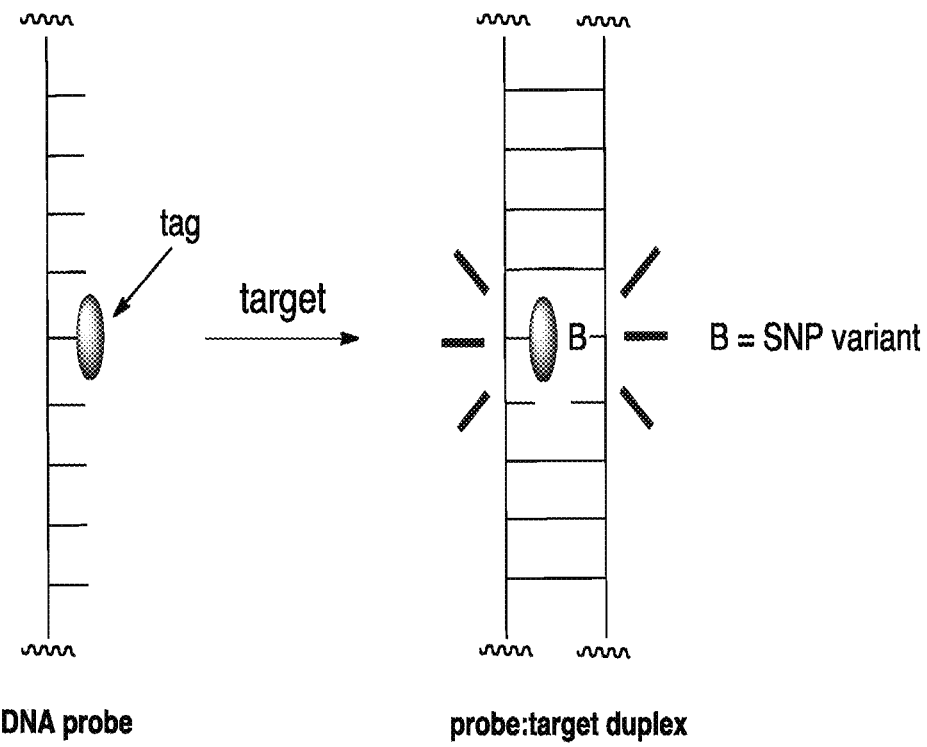

FIG. 1—Schematic of the SNP sensing mechanism, whereby the signal response from an attached tag (normally a fluorophore) to duplex formation with a target strand depends upon the identity of the nucleobase opposite (or opposite and adjacent to) the tag.

Figure 2:
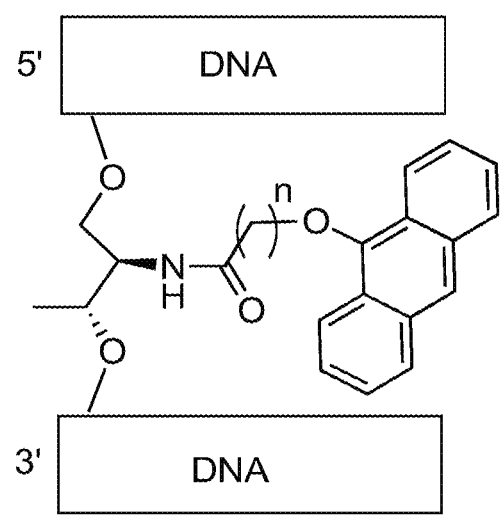

FIG. 2—Schematic of the structure of an anthracene-tagged fluorescent probe. The stereochemistry of the tag is L (R,R). The linker group can be varied, for example n=5.

Figure 3:
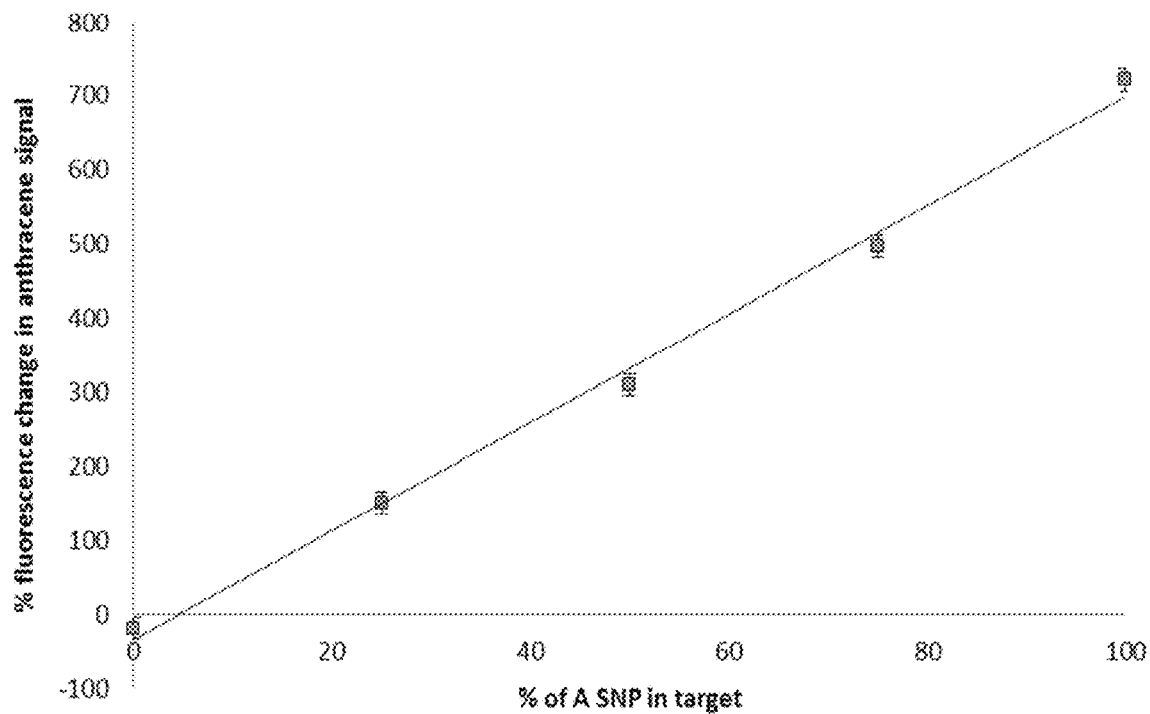

FIG. 3—Calibration of % A variant present versus % change in emission intensity, performed on 1 mL samples with 1 μM probe and 1.5 μM target in 10 mM sodium phosphate buffer pH 7 and 100 mM NaCl, $\lambda_{ex}$=350 nm, 293 K. λex=350 nm, λem=426 nm, rt.

Figure 4:
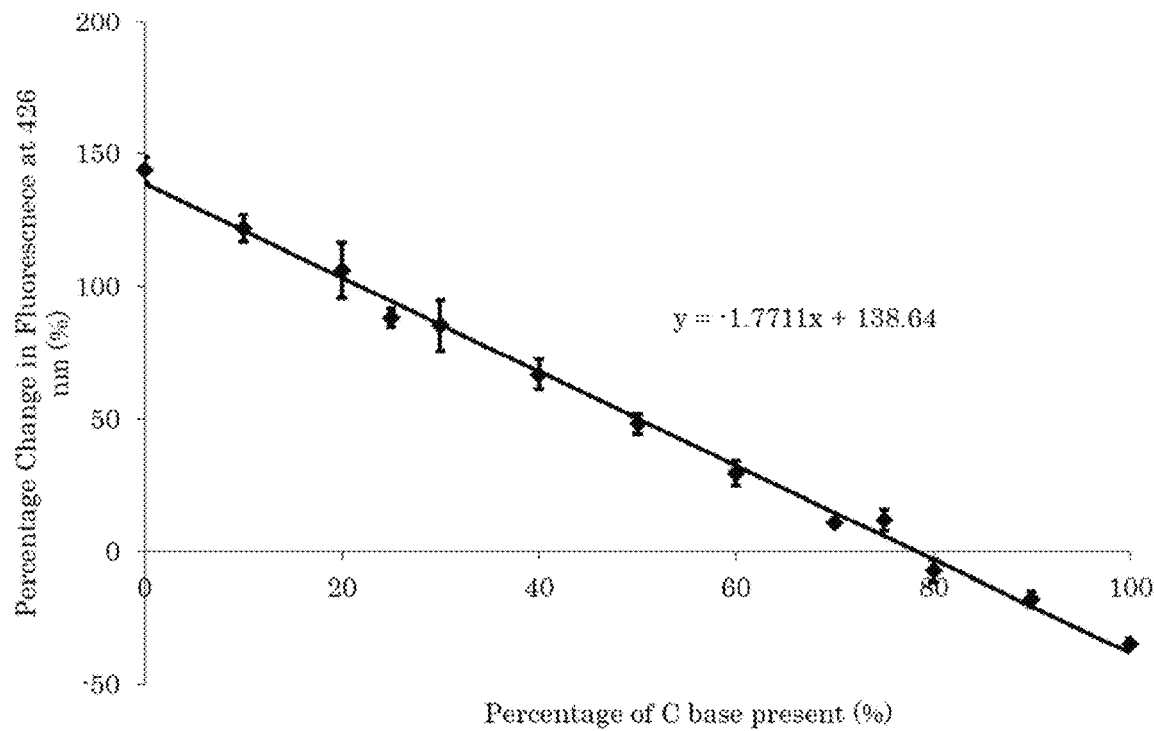

FIG. 4—Calibration of % C variant present versus % change in emission intensity, performed on 1 mL samples with 1 μM probe and 1.5 μM target in 10 mM sodium phosphate buffer pH 7 and 100 mM NaCl, $\lambda_{ex}$=350 nm, 293 K. λex=350 nm, λem=426 nm, rt.

Figure 5:
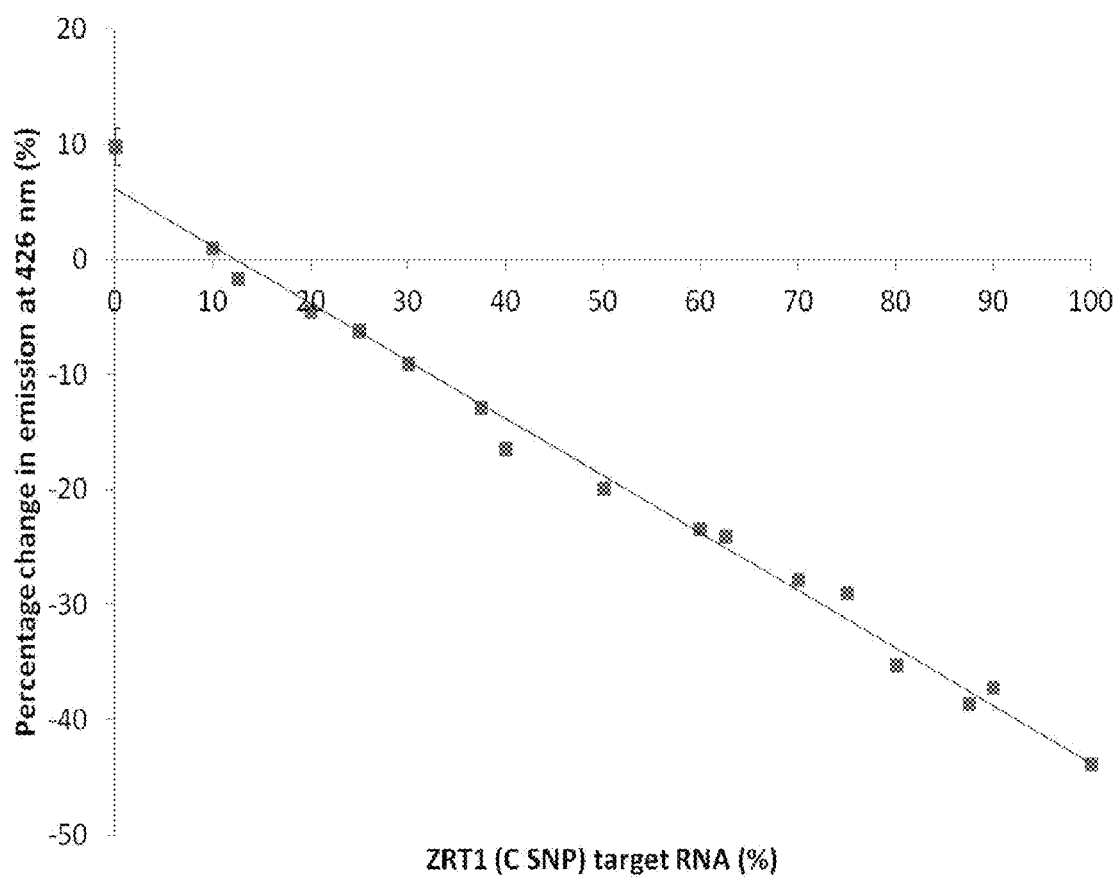

FIG. 5—Calibration of % C variant present versus % change in emission intensity, performed on 1 mL samples with 1 μM probe and 1 μM target in 10 mM sodium phosphate buffer pH 7 and 100 mM NaCl, $\lambda_{ex}$=350 nm, 293 K. λex=350 nm, λem=426 nm, rt.

Figure 6:
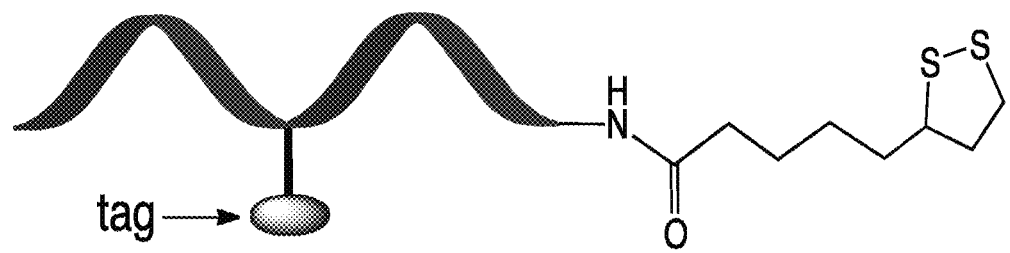

FIG. 6—Anthacene-tagged DNA strands were functionalised with a tether consisting of a 1,2-dithiolane end group (left) by reacting a strand of DNA containing an aminoalkyl group with thiooctic acid under standard peptide coupling conditions.

Figure 7:
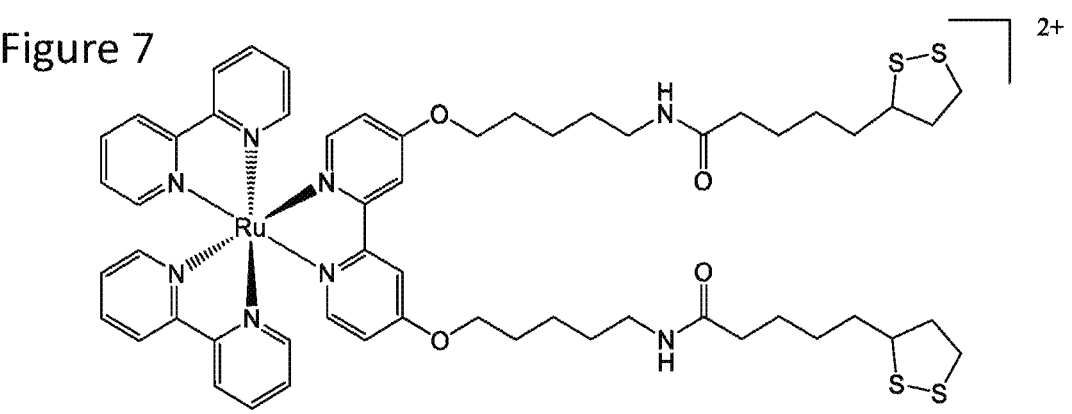

FIG. 7—Shows the structure of the RubpySS probe.

Figure 8A:
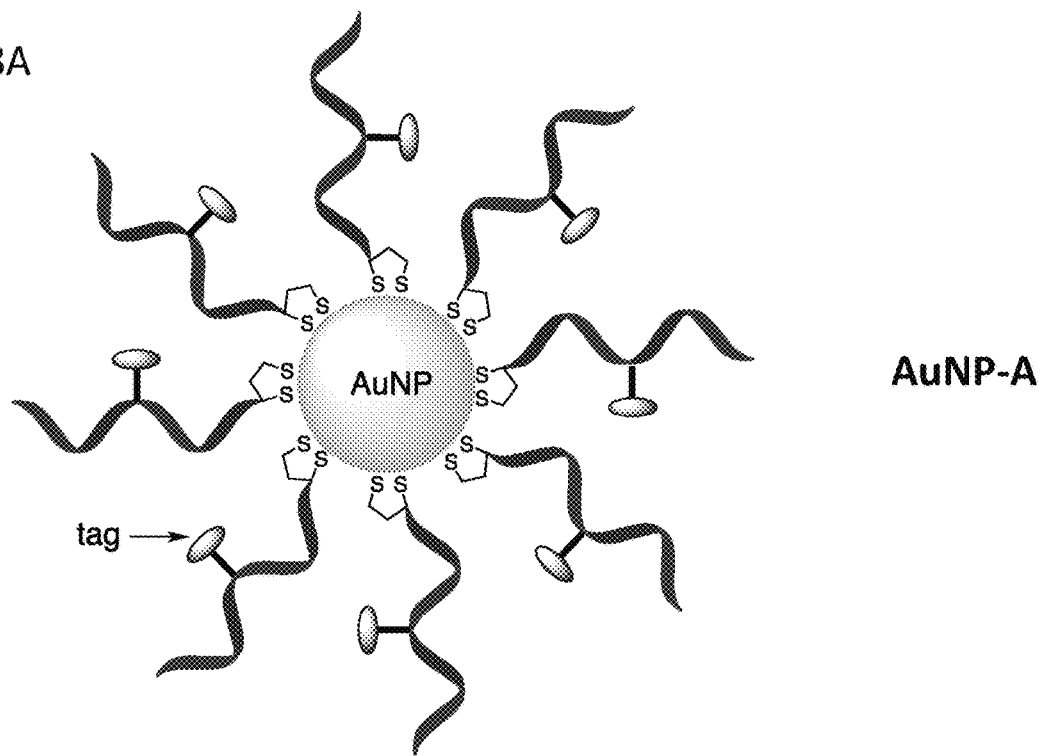
Figure 8B:
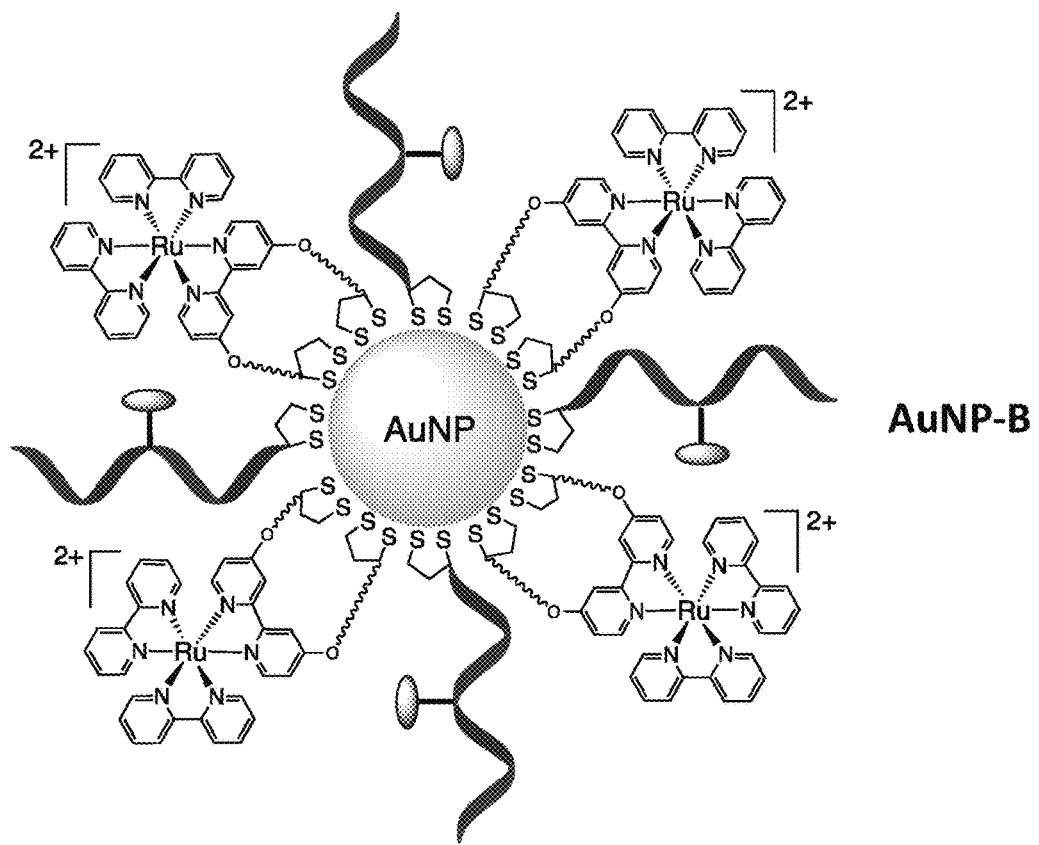

FIG. 8—AuNPs containing (left) DNA-dithiolane strands, AuNP-A, and (right) both DNA-dithiolane strands and Ru(bipy)$_3$-tagged bis-dithiolane molecules, AuNP—B, for ratiometric sensing.

Figure 9:
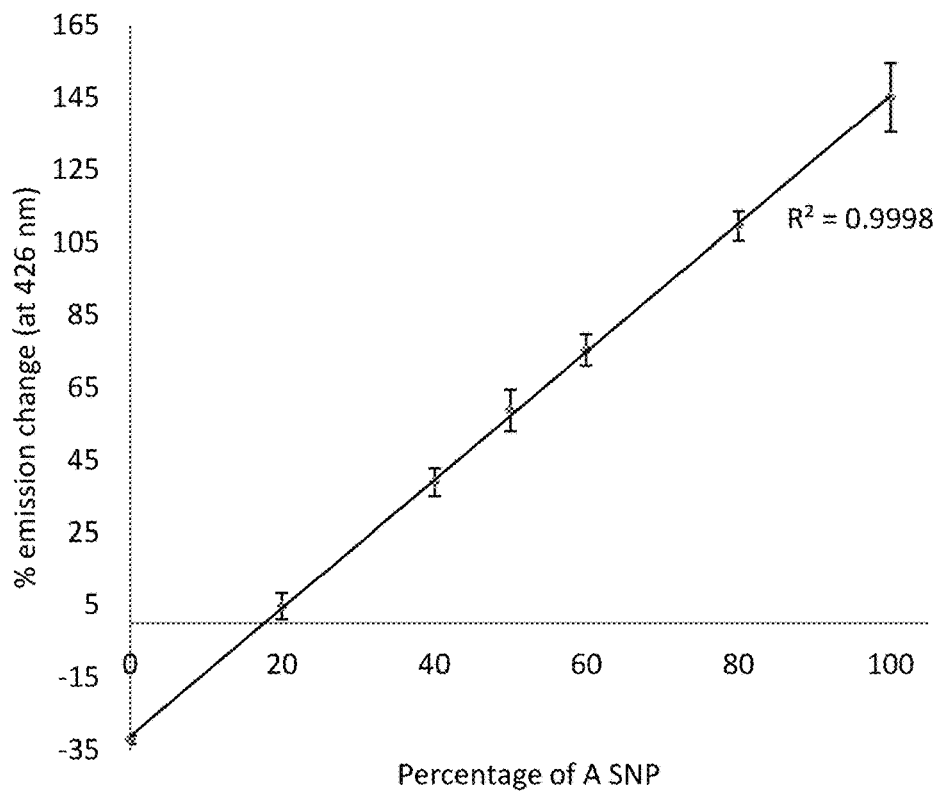

FIG. 9—Calibration of % A variant present versus % change in emission intensity using AuNP-A particles. Error bars are standard deviation of three repeats with three separate AuNP syntheses at RT. $\lambda_{ex}$=350 nm, $\lambda_{em}$=426 nm.

Figure 10:
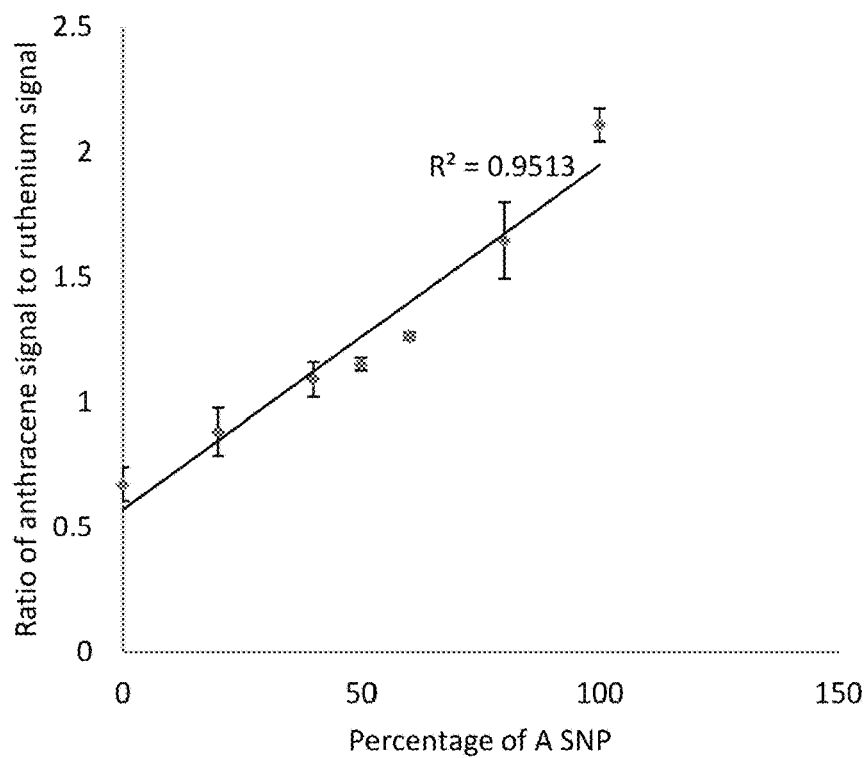

FIG. 10—Calibration of % A present versus ratio of anthracene signal (426 nm)/ruthenium signal (630 nm) for Au—NP—B. Error bars are standard deviation of three repeats at RT.

Figure 11:
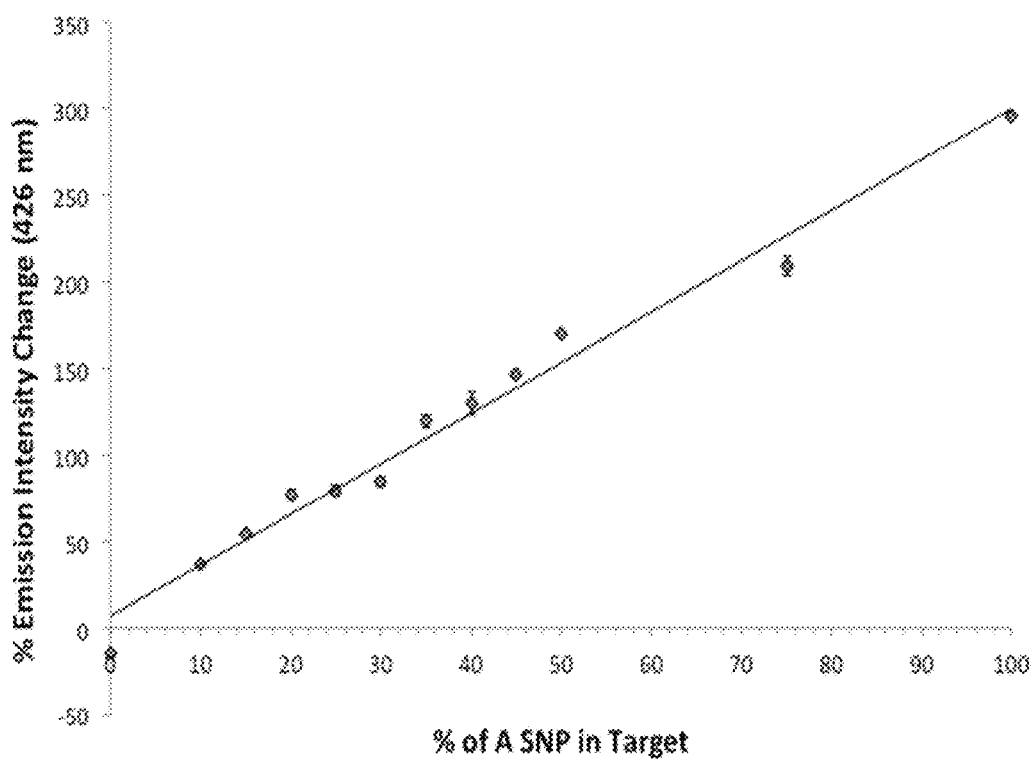

FIG. 11—Percentage change in fluorescence of 173 base synthetic oligonucleotide strands once fully hybridised with the 5 L-anthracene tagged oligonucleotide probe. The error bars are the standard deviation from 3 repeats. 1 μM of target with 1 μM of probe and that is able to detect the A/T SNP difference in a BRAF gene.

Figure 12:
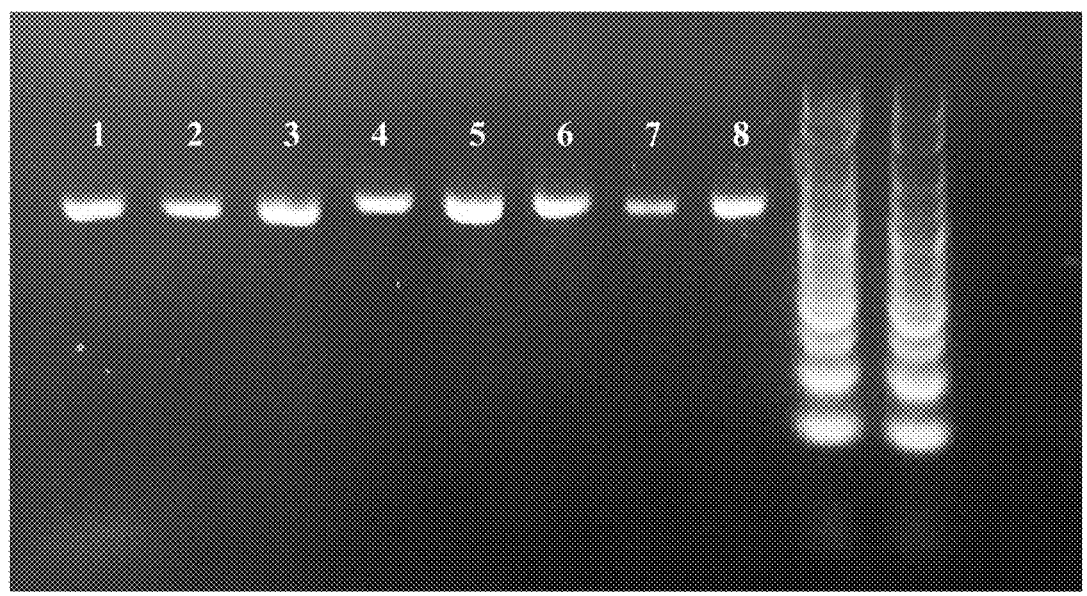

FIG. 12—3% agarose gels to show the ~150 base pair PCR product. The gels represent two different PCRs. Gel A: Lanes 1-4 show the PCR product of the genomic DNA from tumour tissue and lanes 5-8 show the PCR product of the genomic DNA from healthy tissue.

FIG. 13—Sequencing data of the PCR product from the genomic DNA from healthy tissue (wild type) (SEQ ID NO: 21, SEQ ID NO: 22).

FIG. 14—Sequencing data of the PCR product from the genomic DNA from tumour tissue (SEQ ID NO: 23, SEQ ID NO: 24, SEQ ID NO: 25).

Figure 15:
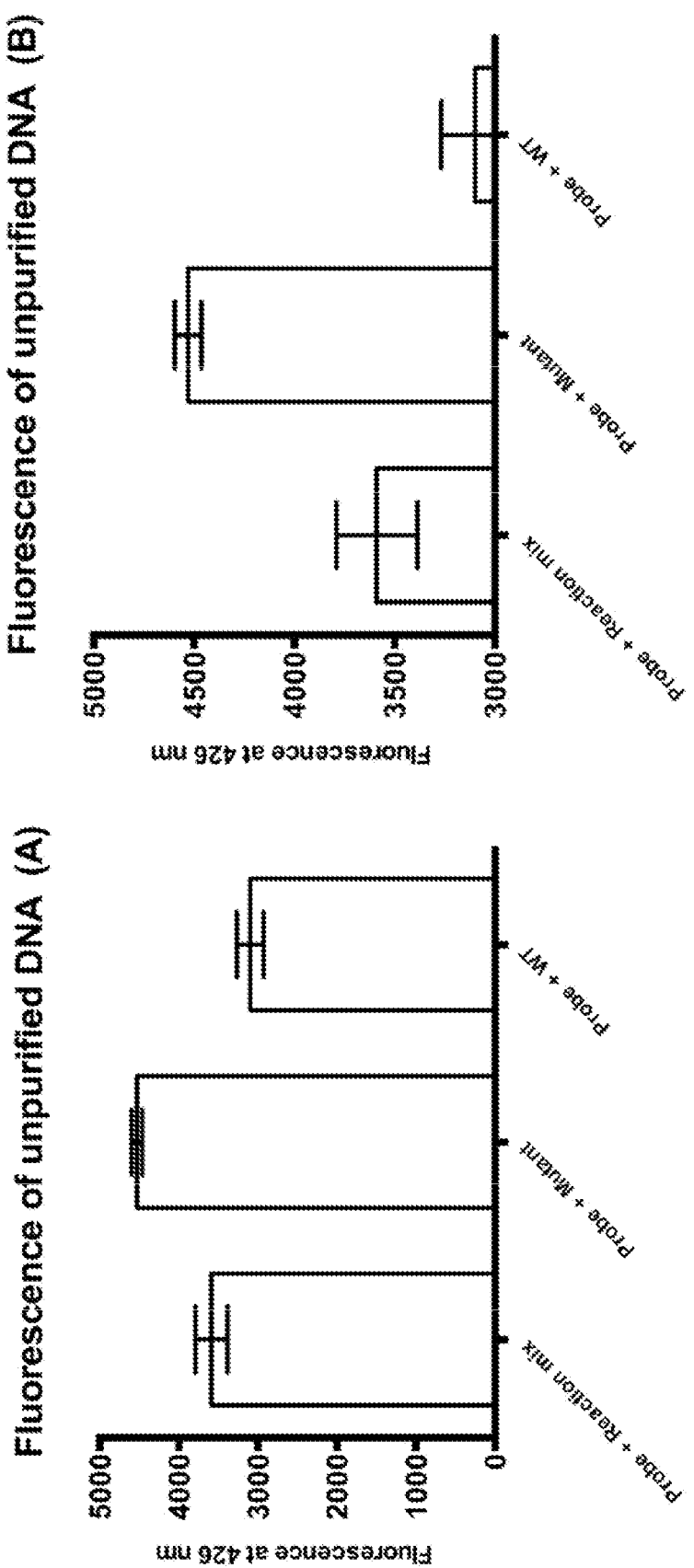

FIG. 15—Graph (A) shows the full fluorescence emission intensity at 426 nm of the unpurified PCR product samples when added to the probe 5'-AGATTTCXCTGTAGC-3' (SEQ ID NO: 2) (BRAF, X=anthracene 5 L, 1 μM); Graph (B) shows the data focused between 3000 and 5000 units to demonstrate the difference between each sample more clearly. The error bars show the standard deviation from 3 experimental repeats.

EXAMPLES

Example 1—Preparation of Genetic Probe

Anthracene Probe Synthesis

Synthesis of 2-(anthracen-9-yloxy) acetate

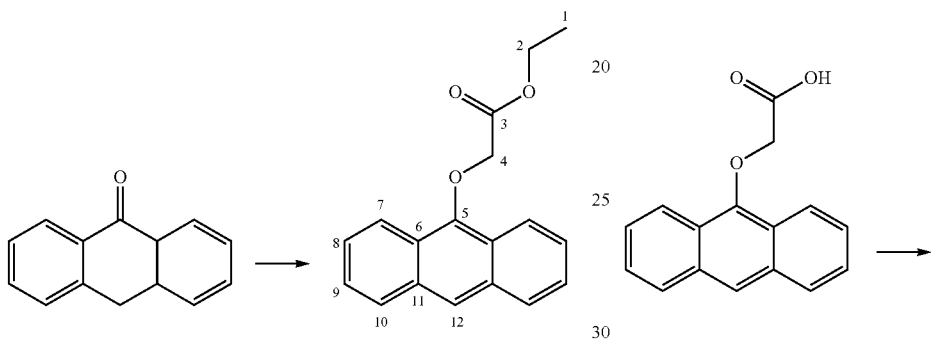

In a round bottomed flask anthrone (5.83 g) and $K_2CO_3$ (4.15 g) were dissolved in degassed acetone (200 mL) and stirred for 15 minutes in the dark. Ethyl Bromoacetae (3.3 mL) was then syringed into the flask and the reaction refluxed under $N_2$ overnight in the dark. The solution was filtered to remove the $K_2CO_3$ and the solvent removed in vacuo. The solid was re-dissolved in DCM (100 mL) and washed with water (50 mL) before drying with $MgSO_4$. The solvent was removed by reduced pressure and the solid (compound 2) purified by column chromatography (10% hexane: DCM) giving a yellow solid (1.91 g, 23%).

Rf=0.54 in 10% hexane: DCM; $^1$HNMR (300 MHz, CDCl$_3$) δ 8.23 (2H, d, J 8.5, H$_7$), 8.09 (1H, s, H$_{12}$), 7.84 (2H, d, J 8.1, H$_{10}$), 7.28-7.44 (4H, m, H$_8$ H$_9$), 4.66 (2H, s, H$_4$), 4.24 (2H, q, J 7.1, H$_2$), 1.23 (3H, t, J 7.1, H$_1$);
TOF-MS-ES$^+$ [M+H]$^+$ 281.12 [M+Na]$^+$303.09

Synthesis of 2-(anthracen-9-ylox) Acetic Acid

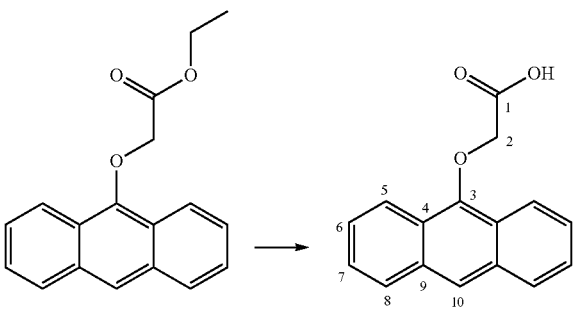 [SMILES: CCOC(=O)COc1c2ccccc2cc2ccccc12 ; O=C(O)COc1c2ccccc2cc2ccccc12]

In a round bottomed flask, 1 g of 2-(anthracen-9-yloxy) acetate was dissolved in 10% NaOH in EtOH 1:1 (200 mL), this was refluxed overnight in the absence of light under $N_2$. The EtOH was removed in vacuo and water was added (400 mL), conc HCl was then added dropwise whilst swirling the solution until a creamy precipitate appears and does not disappear upon mixing, to give a cream solid (800 mg, 89%).

$^1$HNMR (300 MHz, CDCl$_3$) δ 8.34 (1H, s, H$_{10}$), 8.31 (2H, d, J 8.3, 2×H$_8$), 8.06 (2H, d, J 8.0, 2×H$_8$), 7.49-7.60 (4H, m, 2×H$_6$, H$_7$), 4.91 (2H, s, H$_2$); $^{13}$CNMR (100 MHz, CDCl$_2$) 172.1 (C$_1$), 149.5 (C$_3$), 132.6 (2×C$_9$), 128.9 (2×C$_8$), 127.2 (2×C$_6$), 126.1 (2×C$_7$), 125.7 (2×C$_6$), 123.6 (C$_{10}$), 121.6 (2×C$_8$), 71.2 (C$_2$);
TOF-MS-ES$^-$ [M–H]$^-$ 251.06

Synthesis of 2-(anthracen-9-yloxy)-N-((2S,3S)-1,3-dihydroxybutan-2-yl)acetamide

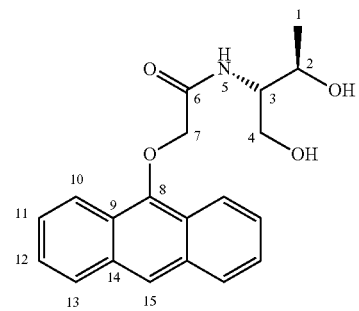

In a round bottomed flask the 2-(anthracen-9-ylox) acetic acid (300 mg) was dissolved in dry DMF (20 mL) under inert conditions. 2-(1H-benzotriazol-1-yl)-1,1,3,3-tetramethyluronium hexafluorophosphate (HBTU) (0.455 g) was added and the solution stirred for 15 minutes in the dark. L-threoninol (0.126 g) and DIPEA (0.21 mL) were added and the solution stirred at 40° C. for 40 hours. The solvent was removed in vacuo the product was then purified by column chromatography (5% MeOH:DCM) giving a pale yellow solid (203 mg, 49%).

Rf=0.27 in DCM: 5% MeOH; $^1$HNMR (300 MHz, CDCl$_3$) δ 8.38 (1H, s, H$_{15}$), 8.30-8.35 (2H, m, H$_{10}$), 8.06-8.11 (2H, dd J 8.4 & 2.0, H$_{13}$), 7.49-7.60 (4H, m, H$_{11}$, H$_{12}$), 4.74 (2H, d, J 5.8, H$_7$), 4.15-4.23 (1H, m, H$_2$), 4.07-4.14 (1H, m, H$_3$), 3.83 (2H, m, H$_4$), 1.35 (3H, d, J 6.4, H$_1$); $^{13}$CNMR (100 MHz, CDCl$_3$) δ 132.1 (C$_{14}$), 128.3 (C$_{13}$), 125.7 (C$_{11}$), 125.3 (C$_{12}$), 124.0 (C$_9$), 122.9 (C$_{15}$), 121.1 (C$_{10}$), 73.2 (C$_7$), 65.6 (C$_2$), 61.6 (C$_4$), 55.8 (C$_3$), 19.3 (C$_1$);
TOF-MS-ES$^+$ [M+Na]$^+$362.1

Synthesis of Anthracene-Tagged Fluorescent Probes

The probes were synthesised using standard phosphoramidite automated DNA synthesis, purified by MS and characterised by mass spectrometry (ESMS).

The stereochemistry of the tag in each case was L (R,R), with the linker group as n=5 (see below). Each probe was a 15-mer, with the eighth position occupied by the anthracene tag.

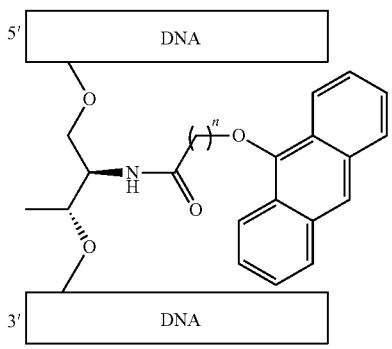

The anthracene probe used for this work is a randomly designed 15-mer which will not display any secondary structure. P.UM is probe sequence; P.AF is probe sequence with thioctic acid modification. The probe strands (P.UM, P.AF, P.1L and P.1D) are the strands that are bound to the gold nanoparticles and used to detect the target strands (DNA-T.1, DNA-T.2).

Each strand was synthesised on an Applied Biosystems 9394 DNA/RNA Synthesizer within the group. They were purified by reverse phase HPLC and characterised by mass spectrometry.

DNA Synthesis with Amine-Termination

The DNA was first modified with an amine group to which the activated ester could be coupled. A 5' amine C6 modification was added as the final base on the DNA synthesiser, giving an amine-terminated probe strand.

Sequences were synthesised on an Applied Biosystems 394 DNA/RNA synthesizer as per normal oligo synthesis, using standard Syn Base CPG 1 μM (Link Technologies).

The 2-(anthracen-9-yloxy)-N-((2S,3S)-1,3-dihydroxybutan-2-yl)acetamide was integrated into the oligonucleotide backbone via the threoninol unit.

Base de-protection was performed off column, in 1M ammonia heated to 55° C. for 6 hours using a heating block (Grant Instruments). The ammonia is removed under reduced pressure.

The sequences were then purified by semi-prep HPLC (Dionex UVD 1705) using a Clarity 5p Oligo-RP 150×4.6 mm (Phenomenex) column. After collecting the purified peak, the solvent is removed in vacuo (Thermo Scientific SAVANT SPD 131 DDA) before dissolving in water and passing through a NAP-10 column (GE Healthcare). The samples were then characterised by Mass Spectrometry and analytical HPLC (Shimadzu UFLC) on a Clarity 5p Oligo-RP 150×4.6 mm 5 micron (Phenomenex) column.

RNA Synthesis with Amine-Termination

Sequences were synthesised on an Applied Biosystems 394 DNA/RNA synthesizer as per standard RNA oligo synthesis, using standard RNA bases (Link Technologies). The sequences were left on column after the synthesis; columns were then removed from the synthesiser and washed with 2.5 mL ammonia:ethanol (3:1) using syringes, washing through every 30 minutes for 2 hours. The mixture was then poured into a vial, washing the column once more with 1 mL ammonia:ethanol (3:1). The solution was then heated for 6 hours at 55° C. Once cooled, the solution was dried on a rotor evaporator. The dry sample was vortexed in 0.5 mL of TBAF (1 M in THF) and left overnight.

The samples were then passed through a NAP-10 column (GE Healthcare) using water as eluent. The solution was then concentrated, 375 mL of sample was placed into a 2 mL Eppendorf, to this 0.2 mL of Sodium acetate (0.1 M) and 1.4 mL of iso-propanol were added. The mixture was centrifuged in a refrigerated centrifuge at 15000 rpm at 4° C. for 15 minutes. The supernatant was removed in a speed vac, the pellets were recombined in 1 mL water, vortexing to re-dissolve them. The samples were then purified by semi-prep HPLC using a Clarity 5μ Oligo-RP 150×4.6 mm column. The solvent was then removed and the samples passed through a NAP-10 column to desalt. The samples were then characterised by Mass Spectrometry and analytical HPLC on a Clarity 5μ Oligo-RP 150×4.6 mm 5 micron column.

Synthesis of 2,5-dioxopyrrolidin-1-yl 5-(1,2-dithiolan-3-yl)pentanoate=NHS Ester of Thioctic Acid

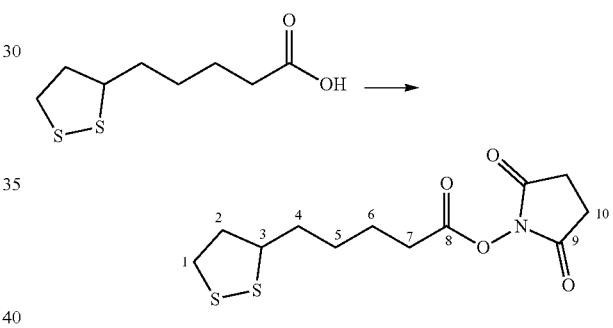

In a round bottomed flask 1.84 g N-(3-Dimethylaminopropyl)-N'-ethylcarbodiimide hydrochloride was dissolved in anhydrous DCM (20 mL). 1.7 mL of N,N-Diisopropylethylamine (DIPEA) was added the reaction and the reaction was allowed to stir for 10 minutes. The reaction vessel was placed in an ice bath before 1.29 g of N-Hydroxy succinimide (NHS) was added to the mixture and allowed to stir. 1.643 g of thioctic acid was firstly dissolved in 10 mL of anhydrous DCM, then added to the reaction over 5 minutes. The reaction was then left to stir overnight at room temperature. The reaction was washed with HCl (aq) (5% [v/v], 50 mL) twice and then with 50 mL water. The organic layer was dried over $Na_2SO_4$ and then solvents concentrated in vacuo. The residue was dry loaded onto $Na_2SO_4$ and purified by column chromatography (50% EtAc:50% Hexane) giving the purified product (compound 1) as a yellow powder (0.451 g, 1.49 mmol, 19%).

Rf=0.57 in EtAc:Hexane 50:50; $^1$HNMR (300 MHz, DMSO) δ 3.56-3.65 (1H, m, $H_3$), 3.12-3.21 (2H, m, $H_{10}$), 2.81 (4H, s, $H_{10}$), 2.69 (2H, t, J 7.1, $H_7$), 2.38-2.46 (1H, m, $H_2$), 1.84-1.93 (1H, m, $H_2$), 1.4-1.7 (6H, m, $H_4$ $H_5$ $H_6$); $^{13}$CNMR (100 MHz, DMSO) δ 170.2 (2×$C_9$), 168.9 ($C_8$), 55.9 ($C_3$), 40.1 ($C_2$), 38.1 ($C_1$), 33.8 ($C_4$), 30.0 ($C_7$), 27.6 ($C_5$), 25.4 (2×$C_{10}$), 24.0 ($C_6$), TOF MS EI$^+$ [M]$^+$303.09

Coupling Oligonucleotide to Thioctic Acid Binding Agent

Amine-modified oligonucleotide was dissolved in sodium carbonate buffer (100 μL, 0.1 M). A 5 molar excess of the NHS ester of thioctic acid was added dissolved in DMSO (5 μL).

The reaction was vortexed and heated overnight at 37° C. The reaction was then passed through a NAP-5 column (GE Healthcare) using TEAA buffer (0.1 M) as eluent. The modified oligonucleotide was then purified by HPLC and characterised by Mass Spectrometry.

Modifying DNA strand with thioctic acid analogue

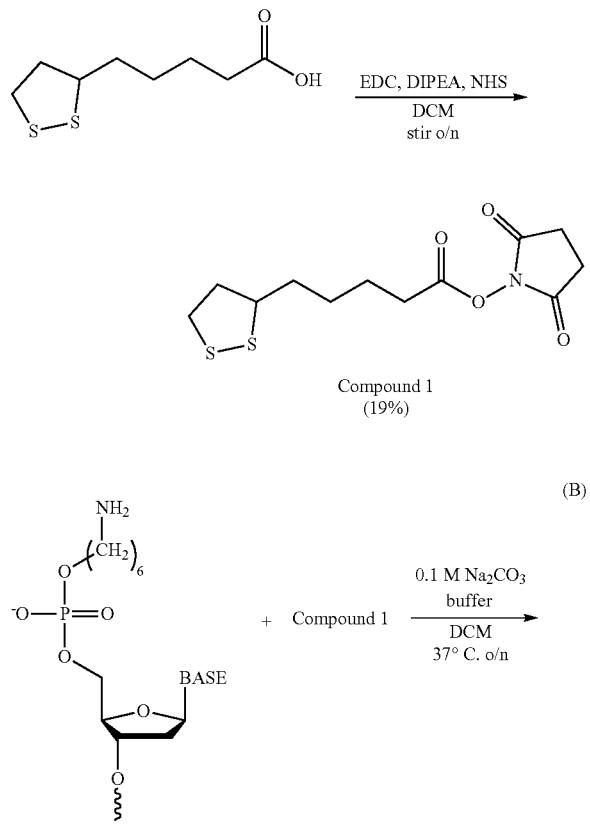

(A) Formation of the activated NHS ester of thioctic acid.
(B) Activated NHS ester is coupled to amine modified DNA strand Thioctic Acid Phosphoramidite Synthesis Synthesis of 5-(1,2-dithiolan-3-yl)-N-(2-hydroxyethyl)pentanamide (Compound 7)

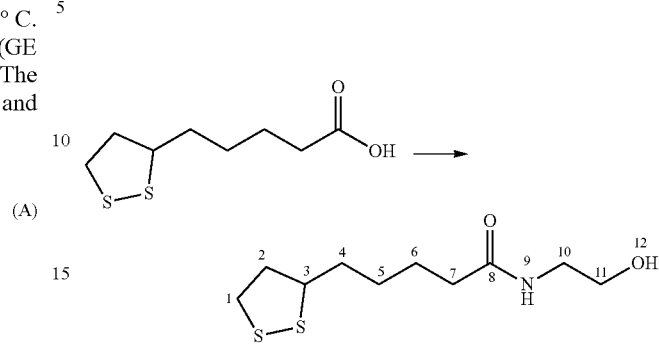

In a round bottomed flask, thioctic acid (0.71 g) and HOBt (0.46 g) were dissolved in dry DMF (10 mL) and stirred over ice. To this, EDC·HCl (0.66 g) was added and the mixture was stirred for 1 hour, still over ice. The solution was allowed to warm to room temperature for 1 hour. In a separate flask, 4-ethylmorpholine (0.39 g) and 2-aminoethan-1-ol (0.15 g) was dissolved in dry DMF (5 mL), this was then added to the thioctic acid containing solution and then allowed to stir overnight. The solution was washed with DCM:$H_2O$, the DCM was then removed under reduced pressure. The product was purified by column chromatography on silica (5% MeOH, $CHCl_3$) giving the product as a yellow solid (455 mg, 73%).

Rf=0.41 in $CHCl_3$: 5% MeOH; $^1$HNMR (300 MHz, $CDCl_3$) δ 6.57 (1H, s, $H_9$), 3.58-3.77 (2H, m, $H_{11}$), 3.45-3.56 (1H, m, $H_3$), 3.28-3.40 (2H, m, $H_{10}$), 3.20-2.97 (2H, m, $H_1$), 2.40 (1H, dq, J 12.6, 6.1, $H_2$a), 2.16 (2H, t, J 7.3, $H_7$), 1.85 (1H, dq, J 13.2, 6.7, $H_{8b}$), 1.52-1.72 (4H, m, $H_4$ $H_6$), 1.33-1.45 (2H, m, $H_5$); $^{13}$CNMR (100 MHz, $CDCl_3$) δ 174.2 ($C_8$), 61.9 ($C_{11}$), 56.4 ($C_3$), 42.4 ($C_{10}$), 40.3 ($C_2$), 38.5 ($C_1$), 36.3 ($C_7$), 34.6 ($C_4$), 28.9 ($C_5$), 25.4 ($C_6$);
TOF-MS-ES$^+$[249.1]$^+$

Synthesis of 2-(5-(1,2-dithiolan-3-yl)pentanamido)ethyl (2-cyanoethyl) diisopropylphosphoramidite (Compound 8)

In a round bottomed flask, the 5-(1,2-dithiolan-3-yl)-N-(2-hydroxyethyl)pentanamide (125 mg) was dissolved in dry DCM (5 mL) under an inert atmosphere. To this DIPEA (0.716 mL) was added. (i-Pr$_2$N)PClO(CH$_2$)$_2$CN (0.314 mL) was added dropwise to the reaction mixture, the reaction was then left to stir for 2 hours. Once the reaction was complete, degassed EtAc (5 mL) was added, the solution was then washed with degassed Na$_2$CO$_3$ (2 M, 2×50 mL) then degassed brine (50 mL) before being dried over Na$_2$SO$_4$. The solution was filtered and dried under reduced pressure before being purified by column chromatography on activated alumina (EtAc:Hexane:TEA, 50:49:1) giving a yield of 75%.

Rf; 0.9; $^1$HNMR (300 MHz, CD$_3$CN) δ 3.44-3.90 (7H, m, H$_3$ H$_{11}$ H$_{12}$ H$_{14}$) 3.34-3.44 (2H, m, H$_{10}$) 2.99-3.17 (2H, m, H$_1$) 2.60 (2H, t, J 6.2, H$_{15}$) 2.40 (1H, dtd, J 12.9, 6.6, 5.5, H$_2$) 2.13 (2H, t, J 7.5, H$_7$) 1.84 (1H, dq, J 12.7, 7.0, H$_2$) 1.5-1.73 (4H, m, H$_4$ H$_6$) 1.33-1.47 (2H, m, H$_5$) 1.12 (12H, dd, J 6.9, 4.6, H$_{13}$); $^{13}$CNMR (100 MHz, CD$_3$CN) 173.0 (C$_8$), 117.8 (C$_{16}$), 62.5 (C$_{11}$), 58.9 (C$_{14}$), 56.9 (C$_3$), 54.6 (C$_7$), 43.3 (C$_{22}$), 40.6 (C$_{10}$), 38.8 (C$_2$), 36.1 (C$_1$), 34.8 (C$_4$), 29.0 (C$_5$), 25.6 (C$_6$), 24.6 (C$_{13}$), 20.4 (C$_{15}$); $^{31}$PNMR (120 MHz, CD$_3$CN) δ 148.0;

TOF-MS-ES$^+$ [M+H]$^+$ 450, [M+Na]$^+$472.

Synthesis of ruthenium-4,4'-Di(5-lipoamido-1-pentoxy)-2,2'-bi-pyridine (RubpySS)

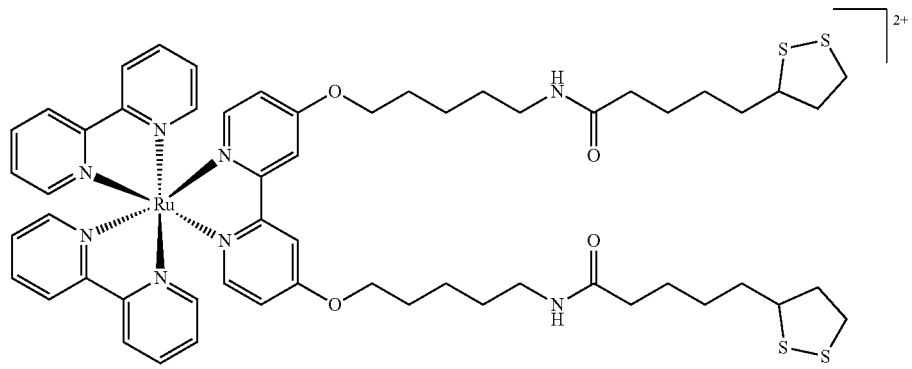

The ruthenium based probe, ruthenium-4,4'-di(5-lipoamido-1-pentoxy)-2,2'-bi-pyridine (RubpySS) was synthesised in accordance with Adams, S. J., et al, ACS Appl. Mater. Interfaces 6, 11598-11608 (2014).

Coupled Oligonucleotides

| Probe | Sequence | Mass Spec ES+ |
|---|---|---|
| P.UM | TGG ACT CTC TCA ATG (SEQ ID NO: 3) | 4696 [M + H]$^+$ |
| P.AF | W-TGG ACT CTC TCA ATG (SEQ ID NO: 4) | 4911 [M]$^+$ |
| P.1L | W-TGG ACT CLC TCA ATG (SEQ ID NO: 5) | 5008 [M]$^+$ |
| P.1D | W-TGG ACT CDC TCA ATG (SEQ ID NO: 6) | 5008 [M]$^+$ |
| P.5L | W-CAU UGA GXG AGU CCA (SEQ ID NO: 7) | 5065 [M]$^+$ |
| m.P.1L | W-AAAAA TGG ACT CLC TCA ATG (SEQ ID NO: 8) | 6573 [M − H]$^-$ |
| l.P.1L | W-AAAAA AAAAA TGG ACT CLC TCA ATG (SEQ ID NO: 9) | 8139 [M − H]$^-$ |
| DNA-T.1 | CAT TGA GAG AGT CCA (SEQ ID NO: 10) | 4601 [M + H]$^+$ |
| DNA-T.2 | CAT TGA GAA AGT CCA (SEQ ID NO: 11) | 4585 [M] |
| RNA-T.1 | CAU UGA GAG AGU CCA (SEQ ID NO: 12) | 4798 [M − H]$^-$ |
| RNA-T.2 | CAU UGA GAA AGU CCA (SEQ ID NO: 13) | 4782 [M − H]$^-$ |
| DNA-T.3 | AGC TGA GAC GCG ACT (SEQ ID NO: 14) | 4602 [M] |
| DNA-T.4 | AGC TGA GCC GCG ACT (SEQ ID NO: 15) | 4577 [M − H]$^-$ |
| RNA.1 | Q-CAA UCA GGG UCG ACG AGA A (SEQ ID NO: 16) | 6458 [M] |
| RNA.2 | UUC UCG UCG ACC CUG AUU G (SEQ ID NO: 17) | 5952 [M] |

W = thioctic acid modification
L = 1L anthracene probe
D = 1D anthracene probe
X = 5L anthracene probe
Q = Compound 8 modification The numbers 1 or 5 refer to the carbon linker length between the anthracene molecule and the threoninol unit. The L and D indicate the isomer of threoninol used in the synthesis.

Gold Nanoparticle (AuNP) Synthesis

Particles are grown by the particle seeding method starting with 13 nm particles, which are synthesised as described below. Initially stock solutions of the reactants were made up as: 5 mM HAuCl$_4$·H$_2$O (100 mg in 50 mL deionised H$_2$O), 57 mM ascorbic acid (500 mg in 50 mL deionised H$_2$O) and 34 mM trisodium citrate dehydrate (500 mg in 50 mL deionised H$_2$O).

13 nm Gold Nanoparticles

All glassware was soaked in aqua regia for at least 30 minutes prior to reaction, the glassware was then rinsed 10 times with deionised water and placed in an oven prior to use. In a 250 mL round bottomed flask fitted with a condenser, 100 mL of 2.75 mM citrate buffer (75:25 sodium citrate:citric acid) was heated until boiling, ensuring a vortex is formed by the vigorous stirring. After 15 minutes of boiling, 1.6 mg of Ethylenediaminetetraacetic acid (EDTA) was added to the solution. In a separate flask, 25 mL of HAuCl$_4$·3H$_2$O (Sigma Aldrich) (8.5 mg) is placed in an oven to heat until 90° C. The solution of gold was then added rapidly to the centre of the vortex of the citrate buffer solution and allowed to boil for 20 minutes. After 20 minutes the heat is turned off, and the solution is allowed to cool to room temperature still with vigorous stirring.

SPR=519 nm, number distribution=12 nm (±3 nm), intensity distribution=21 nm (±6 nm)

25 nm Gold Nanoparticles

A solution of 30 mL 13 nm AuNP (2 nM) was diluted to 40 mL with deionised water in a 250 mL three necked round bottomed flask. The solution was vigorously stirred. Two solutions were then made up using the stock solutions, solution A=1 mM HAuCl$_4$·H$_2$O (20 mL) solution B=2.85 mM ascorbic acid and 1.7 mM trisodium citrate dehydrate (20 mL). Solution A and B were then added to the AuNP solution using a peristaltic pump over 45 mins. Once added, the AuNP solution was refluxed for 30 minutes and allowed to cool to room temperature.

Number distribution=22 nm (±5 nm), intensity distribution=31 nm (±8 nm)

50 nm Gold Nanoparticles

A solution of 9 mL 25 nm AuNP (0.7 nM) was diluted to 40 mL with deionised water in a 250 mL three necked round bottomed flask. The solution was vigorously stirred. Two solutions were then made up using the stock solutions, solution A=1 mM HAuCl$_4$·H$_2$O (20 mL) solution B=2.85 mM ascorbic acid and 1.7 mM trisodium citrate dehydrate (20 mL). Solution A and B were then added to the AuNP solution using a peristaltic pump over 45 mins. Once added, the AuNP solution was refluxed for 30 minutes and allowed to cool to room temperature, the solution was neutralised with 0.01 M NaOH.

Number distribution=38 nm (±9 nm), intensity distribution=56 nm (±16 nm)

100 nm Gold Nanoparticles

A solution of 40 mL 50 nm AuNP (80 pM) was placed in a 250 mL three necked round bottomed flask. The solution was vigorously stirred. Two solutions were then made up using the stock solutions, solution A=4 mM HAuCl$_4$·H$_2$O (20 mL) solution B=11.4 mM ascorbic acid and 3.4 mM trisodium citrate dehydrate (20 mL). Solution A and B were then added to the AuNP solution using a peristaltic pump over 45 mins. Once added, the AuNP solution was refluxed for 30 minutes and allowed to cool to room temperature.

SPR=561 nm, number distribution=68 nm (±20 nm), intensity distribution=105 nm (±32 nm) (100%)

Characterising AuNP

Sizing 1 mL of 2 nM AuNP sample is placed into a disposable DT50012 cuvette (SARSTEDT) before sizing the particles on a Zetasizer NANO (Malvern). Each sample was run 12 times, repeating this 3 times and taking an average of the value.

Transmission Electron Microscopy

Using tweezers to hold the copper grid (3 mm, FORMVAR) in a clean and safe area, 20 μL of 2 nM sample of AuNP is pippeted onto the grid. The sample is left to settle for 20 minutes, after 20 minutes wick away excess using filter paper. The samples were then imaged using a JEOL 1200 Transmission Electron Microscope. Coated AuNP procedure Coating AuNP Procedures Coating 13 nm AuNP with DNA and RubpySS In an Eppendorf containing a magnetic stirrer, citrate coated AuNPs (13 nm, 3 nM) are made up in 10 mM pH 7.0 phosphate buffer. Thioctic acid modified DNA (0.33 μM) is added to the AuNPs and stirred for 2 minutes before the solution is sonicated for 20 seconds. This process is repeated a further two times giving a final DNA concentration of 0.98 μM. RubpySS (1.5 μM) probe is added to the particles and allowed to stir for 20 minutes. This process is repeated, giving a final RubpySS concentration of 3 μM. The particles are passed through a Sephadex G-50 column (stored in 20% ethanol) with deionised water as eluent. A final UV-vis spectrum is taken to confirm concentration.

| Particle | SPR (nm) | Size: number distribution (nm) | Size: intensity distribution (nm) |
|---|---|---|---|
| P.AF-AuNP-Ru | 524 | 14 (±4) | 40 (±19) 97% |
| P.1L-AuNP-Ru | 524 | 14 (±4) | 34 (±17) 96% |
| P.1D-AuNP-Ru | 524 | 14 (±4) | 23 (±9) 87% |
|  |  |  | 286 (±97) 10% |
| l.P.1L-AuNP-Ru | 524 | 16 (±5) | 36 (±6) 96% |
| P.5L-AuNP-Ru | 524 | 15 (±4) | 35 (±16) 96% |

Coating 100 nm AuNP with P.1L and RubpySS

In an Eppendorf containing a magnetic stirrer, citrate coated AuNPs (100 nm, 40 μM) are made up in 10 mM pH 7.0 phosphate buffer. P.1L (0.25 μM) is added to the AuNPs and stirred for 2 minutes before the solution is sonicated for 20 seconds. This process is repeated a further two times giving a final DNA concentration of 0.75 μM. RubpySS (1.13 μM) probe is added to the particles and allowed to stir for 20 minutes. This process is repeated, giving a final RubpySS concentration of 2.3 μM. The particles are then spun down to form a pellet at 13000 rpm for 90 seconds. The supernatant is removed, with care taken to not disturb the pellet. The particles are re-dispersed in deionised water.

SPR=565 nm, number distribution=73 nm±26 nm, intensity distribution=106±38 nm.

Coating 13 nm AuNP with siRNA and RubpySS

In an Eppendorf containing a magnetic stirrer, citrate coated AuNPs (13 nm, 3 nM) are made up in 10 mM pH 7.0 phosphate buffer. RNA.1 (0.33 μM) is added to the AuNPs and stirred for 2 minutes before the solution is sonicated for 20 seconds. The UV-vis spectrum of the particles is taken prior to purification. This process is repeated a further two times giving a final RNA.1 concentration of 0.98 μM. RubpySS (1.5 μM) probe is added to the particles and allowed to stir for 20 minutes. This process is repeated, giving a final RubpySS concentration of 3 μM. The particles are passed through a Sephadex G-50 column (stored in 20% ethanol) with deionised water as eluent. A final UV-vis spectrum is taken to confirm concentration. The particles are made up in 10 mM pH 7.0 phosphate buffer and 100 mM NaCl. To this solution RNA.2 (0.4 μM) is added.

SPR=524 nm, number distribution=15 nm±3 nm, intensity distribution=30 nm±15 nm.

Fluorescence Testing

A 1 µM solution of the duplex DNA was made up with 10 mM phosphate buffer (pH 7.0) and 100 mM NaCl, the solution is thoroughly mixed using a pipette. For DNA-AuNP samples, 2.5 nM AuNP sample was made up with 10 mM phosphate buffer (pH 7.0) and 100 mM NaCl, the solution is thoroughly mixed using a pipette.

For samples run on Shimadzu RF-5301 PC Spectrofluorophotometer, anthracene $\lambda_{ex}$=350 nm $\lambda_{em}$=370-550 nm, slit widths for excitation were 5 nm and emission 10 nm. Each run dwell time 1.0 second, 1 nm bandwidth 1 accumulation.

For samples run on FLSP920 Times Resolved Spectrometer (Edinburgh), anthracene $\lambda_{ex}$=350 nm $\lambda_{em}$=390-550 nm, slit widths for excitation 5 nm and emission 10 nm. Each run dwell time 1.0 second, 1 nm bandwidth 1 accumulation. For the ruthenium probe, $\lambda_{ex}$=465 nm $\lambda_{em}$=580-800 nm, slit widths for excitation 15 nm and emission 15 nm. Each run dwell time 1.0 second, 3 nm bandwidth 3 accumulations.

Example 2

Read-Out of the Allelic Ratio of Nucleobase Variants in Target Strands of DNA and RNA Using Fluorophore-Tagged Probes 1. Introduction Single Nucleotide Polymorphisms (SNPs), variations in one nucleobase at one site in a particular sequence of genomic DNA, play an important role in the development and prognosis of diseases with a genetic component, including cancer. In clinical research, surgery and diagnostics, there is a need for a method that gives a rapid, cheap and reliable read-out out of the allelic (i.e. SNP) ratio to inform clinical decision making.

Over the past few years, an SNP sensing methodology has developed in which SNP identities can be read-out routinely from target samples of DNA. This approach uses duplex formation (hybridisation), involving a tagged DNA probe to generate a fluorescent signal. However a crucial difference in the approach used in the invention herein is that analysis is based on the strength of the signal generated upon duplex formation, not on how well the duplex forms to give a signal. This means the assay can be done at room temperature and obviates the need to use narrow temperature windows to ensure only one transcript (or transcript product) binds. Published work has so far revealed the results of studies on samples of target strands containing either one nucleobase at a locus (homozygous) or a 50/50 mixture (heterozygous). In all these reports, the sensing signal comes from the fluorescence emission from an anthracene tag on the probe strand either increasing or decreasing at a particular monitoring wavelength (e.g. 426 nm) upon duplex formation, with the intensity of the signal directly depending on the identity of the base opposite (FIG. 1).

The invention herein demonstrates on a series of DNA and RNA sequences that there is a linear dependence in the emission signal as a function of the SNP/ratio in the target, thus allowing the SNP ratio (i.e. allelic ratio) to be calibrated and then read-out for unknown mixtures through a simple measure of the emission intensity at a given wavelength.

The results of sensing studies on short (<20-mer) synthetic DNA and RNA targets are described below in Sections 2 (free probes) and 3 (AuNP-bound probes). Section 4 details studies carried out on longer (>100-mer) targets, including PCR-amplified strands derived from patient samples.

2. Studies on Short (<20-Mer) Synthetic DNA and RNA Targets

This section describes work on sensing two different SNPs, using anthracene-tagged fluorescent probes. The stereochemistry of the tag in each case was L (R,R), with the linker group as n=5 (see FIG. 2). Each probe was a 15-mer, with the eighth position occupied by the anthracene tag.

The probes were synthesised as set out above, using standard phosphoramidite automated DNA synthesis, purified by MS and characterised by mass spectrometry (ESMS).

2.1 DNA Sensing (BRAF Gene Mutation)

```
Probe: 5'-AGATTTCXCTGTAGC-3' (SEQ ID NO: 2)
(BRAF, X =
anthracene 5L)

Target: 3'-TCTAAAGXGACATCG-5' (SEQ ID NO: 20)

SNP: BRAF gene transversion (V600E; X = T to A);
associated with cancer

T_m in values: 45.5 (A); 46 (T) (5 µM duplex in
10 mM sodium phosphate buffer pH 7; 100 mM NaCl).
```

The resulting calibration graph is shown in FIG. 3.

2.2 DNA Sensing (P21 Gene SNP)

```
Probe: 5'-AGTCGCGXCTCAGCT-3' (SEQ ID NO: 1)(Zsuzsa,
X = anthracene 5L)

Target: 3'-TCAGCGCXGAGTCGA-5' (SEQ ID NO: 19)

SNP: P21 gene transversion (rs1801270; C to A);
associated with Alzheimer's Disease T_m values: 60° C. (A), 63° C. (C) (5 µM duplex in
10 mM sodium phosphate buffer pH 7; 100 mM NaCl)
```

The resulting calibration graph is shown in FIG. 4.

Using the calibration, unknown heterozygous samples of C and A target were analysed to determine the percentage of C/A base present. The results were calculated using the equation of the linear correlation shown in FIG. 4. The y value was obtained by calculating the percentage change in fluorescence at 426 nm in relation to the probe alone fluorescence. The results of this trial (see Table 1) are shown to be very close to the actual values of the unknown samples.

TABLE 1

| Percentage Change in Fluorescence at 426 nm (%) | Calculated Percentage of C base present (%) | Actual Percentage of C base present (%) |
| --- | --- | --- |
| +28 | 62 | 60 |
| −37 | 99 | 100 |
| +34 | 59 | 55 |
| 0 | 78 | No target |

The results obtained when no target is present highlights one issue: at the point at which the calibration crosses the x-axis, it would not be clear in a test whether (i) there is no target present in solution or (ii) ~80% of target strands have the C nucleobase variant and 20% have the A. However this is addressed by:

Use of a second probe: An identical assay can be run with a separate probe containing a different linker length to the anthracene tag, a different linker stereochemistry or a different fluorophore. In each case, the intercept with the x-axis would occur at a different C/A ratio value. A dual-probe approach also gives a further verification of the results obtained; and/or Use of a second fluorophore tag on one probe: a second fluorophore simply reads out duplex formation through a change in emission intensity; a separate tag allows a ratiometric method for reading out the SNP variant ratio (see Section 3).

2.3 RNA Sensing (P21 Gene SNP)

```
Probe: 5'-AGTCGCGXCTCAGCT-3' (SEQ ID NO: 1)(Zsu-
zsa,
X = anthracene 5L)

Target: 3'-UCAGCGCXGAGUCGA-5' (SEQ ID NO: 18)

SNP: P21 gene transversion (rs1801270; C to A);
associated with Alzheimer's Disease T_m values: 55.5° C. (A), 57° C. (C) (5 µM duplex in
10 mM sodium phosphate buffer pH 7; 100 mM NaCl)
```

The resulting calibration graph is shown in FIG. 5.

3. Studies on Short (<20-Mer) Synthetic DNA Targets Using Probes Attached to Gold Nanoparticles (Au-NPs)

It is known that DNA can be attached to gold nanoparticles (AuNPs) by modification with sulfur-containing groups allow to surface immobilisation through Au-thiolate bonds. It was decided to immobilise the fluorophore-tagged SNP-sensing strands used in the method of the invention onto AuNPs. This approach provides the advantage that in biological media and upon entering cells, Au—NP-immobilised DNA strands tend to be more resistant to nucleases that would otherwise quickly degrade the DNA. This approach would therefore be useful for probing target species (e.g. mRNA) in biological environments. In addition AuNPs can be tailored with additional luminescent groups for ratiometric sensing. Ratiometric sensing consists of analysing the sensing signal from two separate fluorophores at two distinct wavelengths. Dividing one signal intensity by another obviates the need to determine the initial probe concentration; this both simplifies and facilitates the sensing process, in particular for analysis in cellular environments where probe concentrations would be difficult to determine. Further luminescent groups could be used to facilitate tracking in cells as well.

Anthacene-tagged DNA strands were functionalised with a tether consisting of a 1,2-dithiolane end group (FIG. 6) by reacting a strand of DNA containing an aminoalkyl group with thiooctic acid under standard peptide coupling conditions. AuNPs (ca. 13 nm in diameter) were then functionalised with these strands (AuNP-A, FIG. 8A), with strand immobilisation checked by monitoring changes to the SPR band on the UV/vis spectrum in aqueous media. For the mixed nanoparticles designed to explore ratiometric sensing (AuNP—B, FIG. 8B), a Ru(bipy)$_3$ complex (FIG. 7), with well characterised luminescent properties and containing two 1,2-dithiolane end groups, was used in addition to the DNA strands.

```
Probe: 5'-AGTCGCGXCTCAGCT-3' (SEQ ID NO: 1)(Zsu-
zsa,
X = anthracene 5L)

Target: 3'-TCAGCGCXGAGTCGA-5' (SEQ ID NO: 19)

SNP: P21 gene transversion (rs1801270; C to A);
associated with Alzheimer's Disease
```

```
T_m values (AuNP-A): 57.5° C. (A), 59° C. (C)
(2 nM AuNPs in 10 mM sodium phosphate buffer pH 7;
100 mM NaCl)
```

The resulting calibration graph for AuNP-A is shown in FIG. 9. The resulting calibration graph for AuNP—B is shown in FIG. 10.

The data in FIG. 9 surprisingly show that a linear correlation is also possible for the surface-immobilised probes, with the percentage changes similar to the data for the corresponding free probe (FIG. 4). The graph in FIG. 10 also shows that ratiometric sensing is possible using this methodology.

4. Studies on Longer DNA Strand Targets, Including Those from Patient Samples 4.1 173-Mer Synthetic Targets

```
Probe: 5'-AGATTTCXCTGTAGC-3' (SEQ ID NO: 2)(BRAF,
X = anthracene 5L)

Target: 173-mer containing in middle:
3'-TCTAAAGXGACATCG-5' (SEQ ID NO: 20)

SNP: BRAF gene transversion (V600E; X = T to A);
associated with cancer
```

The fluorescence studies undertaken with varying percentages of the BRAF V600E T-to-A cancer mutation within samples of 15-mer synthetic targets demonstrated a linear dependence (Section 2.1). However it was decided to repeat the experiment on a longer synthetic 173-mer oligonucleotide target since such a length would be a more realistic example of the size of a strand that would be generated through amplification by PCR of genomic DNA from actual patient samples (Section 4.2). Due to the BRAF V600E cancer mutation being normally heterozygous rather than homozygous (i.e. cancerous tissue would not be expected to show more than 50% T-A conversion), more data points were chosen between 0% and 50% A in the sample than between 50% and 100% A. The results are shown below in FIG. 11 and again reveal a linear dependence.

This plot could be used to distinguish the amount of A vs T alleles in a mixture of cells by using the percentage fluorescence change upon binding of the anthracene tagged oligonucleotide probe. For example, if the sample gave a 150% change in fluorescence the amount of the A allele present in the sample would be approximately 47%. As with the 15-mer product (FIG. 3), the A target gave a large increase in emission compared to probe alone. However the percentage increase in emission (ca. 300%) was significantly less than that found for the shorter 15-mer (ca. 700% increase), presumably because unbound (single-stranded) sequences in the 173-mer can fold and interact with the fluorophore tag, which would change its immediate environment to some extent.

4.2. PCR of Genomic DNA

PCR cycles were then performed on patient samples containing either wt DNA (100% T, healthy tissue) or mutated DNA (cancerous tissue). The samples were run on an agarose gel and the results can be seen in FIG. 12. Strong bands demonstrate a good yield, which only came once the conditions of the PCR reaction had been optimised by varying different components.

Once the double stranded PCR products were digested to single stranded DNA (the target strand contained phosphorothioate primers to prevent digestion), the samples were submitted for sequencing. The results can be seen in FIGS.

13 and 14. The SNP position that changes malignant melanomas has been circled within the figure. In wt DNA, the position is occupied by a T base (FIG. 13) (SEQ ID NO: 21, SEQ ID NO: 22), whereas the DNA from the tumour tissue shows both A and T (FIG. 14) (SEQ ID NO: 23, SEQ ID NO: 24, SEQ ID NO: 25) due to the heterozygous nature of the BRAF V600E mutation (vide supra). These results therefore confirmed the correct sequences of single stranded DNA in the PCR products, being either 100% T for DNA from healthy tissue or (presumably) 50% T and 50% A for DNA from fully cancerous tissue.

4.3 Fluorescence Studies of PCR Product

The next task was to determine whether the SNP sensing technique was viable on the samples obtained by PCR amplification of genomic DNA derived from patient samples. The fluorescence studies required at least equimolar concentrations of the BRAF probe and the target PCR product, with ideally an excess of product to ensure full binding of the probe. However it was found that after the PCR cycles, followed by digestion of the strands to ssDNA and then finally purification, the yield had dropped by approximately 85%. Therefore preliminary fluorescence studies were undertaken after the digestion step but without any further purification steps.

Gratifyingly, the data show that whereas binding to wtDNA gives a slight decrease in anthracene emission intensity compared to the probe alone, the tumour tissue DNA gives the expected increase (FIG. 15). The data therefore indicates that the SNP sensing protocol is indeed reproducible on DNA derived from patient samples. However, one unexpected finding was the higher than expected emission intensity of the sample containing the probe alone. Control experiments were undertaken to determine whether the fluorescence increase was due to the PCR by-product or another component of the unpurified PCR mixture; these revealed that the formamide used to deactivate the T7 exonuclease had caused the high fluorescence intensity of the mixture of the probe and the reaction mix (~3600 units) compared to the probe alone in buffer (~1600 units). However, as the results in FIG. 15 show, this issue did not preclude the observation of expected increases and decreases in emission intensity for the samples from cancerous and healthy tissue respectively.

There could be several reasons as to why the increase in fluorescence using the PCR products was not as high as expected from the results with the synthetic sequences, which predicted a ca. 150% increase for the heterozygous (50/50) mixture (FIG. 12). The most likely reason is that given the concentration issues encountered, the PCR target may have not being fully in excess, resulting in some unbound probe in the mixture, reducing the signal intensity. Alternatively, the formamide may have had more of an adverse effect on the anthracene emission intensity in the single stranded probe than the corresponding duplexes. Finally the sample from the cancerous tissue may not have been fully heterozygous (i.e. 50% A and 50% T).

5. Conclusions

These examples have proven that it is possible to quantify SNP (allelic) ratios in target samples of DNA or RNA using a novel hybridization assay that operates through monitoring changes in the emission intensity of a fluorophore-tagged DNA probe upon duplex formation. Quantification comes from a demonstration of a linear dependence of the emission intensity on the SNP ratio in the target strand mixture.

The assay works at room temperature and could be adapted for use on a standard plate reader.

The methodology has been demonstrated for two different medical conditions, Alzheimer's disease and cancer. However, the methodology is, in principle, universal for any SNP combination associated with a medical condition (here the targets studied are both transversions, i.e. C/A and T/A), so long as the two duplexes have significantly different emission profiles and similar stabilities ($T_m$ values).

The findings have also shown that the methodology works for (i) RNA targets as well as DNA targets; (ii) probes immobilized on gold nanoparticle surfaces that may be applied for ratiometric sensing in cellular environments or in blood plasma, for example to target circulating tumour DNA (ctDNA) and (iii) different sequence lengths in the target, from 15-mers to >100-mers.

PCR products derived from actual patient samples have been shown to bring about the same trends.

This methodology could also be used for epigenetic screening purposes (i.e. to establish the Me-C/C ratio within a sample), given that these strands can also discern base modifications (i.e. methylation of cytosine) as well as base changes (Duprey et al., ACS Chem. Biol., 2016, 11, 717-721).

An advantage of this method over other known sequencing or sensing approaches (e.g. RNA-seq, TaqMan,) concerns the assessment of heterozygous nucleic acid samples; currently there is no one method that is quick, cheap and quantitative for accurately determining allelic ratios, either from DNA samples (for example in those arising from regions of cancerous tissue) or from mRNA transcripts. The examples provide evidence that all three of these issues can be addressed by the claimed invention.

The invention claimed is:

1. A genetic probe comprising:
   a nanoparticle;
   an oligonucleotide probe anchored to a surface of the nanoparticle, comprising an oligonucleotide backbone with a tag incorporated therein via a linker group; and
   a reference probe anchored to the surface of the nanoparticle, wherein the reference probe comprises a marker; wherein either (a) the tag is an organic fluorescent tag and the marker is a transition metal-based fluorescent marker; or (b) the tag is a redox-active tag and the marker is a transition metal-based redox-active marker.

2. The genetic probe of claim 1, wherein the nanoparticle is formed by a material selected from: metals, metal oxides, silica, graphene, and quantum dots.

3. The genetic probe of claim 1, wherein the organic fluorescent tag is a planar aromatic or heteroaromatic moiety or wherein the redox-active tag is a planar macrocyclic transition metal complex.

4. The genetic probe of claim 1, wherein the organic fluorescent tag is a thiazine fluorescent dye or a cyanine fluorescent dye or a pyrene fluorescent dye or a xanthene fluorescent dye or an acridine fluorescent dye or an anthracene fluorescent dye or an anthraquinone fluorescent dye.

5. The genetic probe of claim 1, wherein the linker group consists of formula (I):

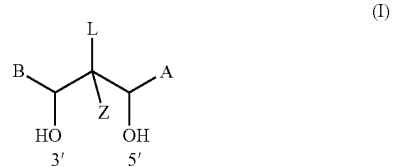

wherein
L is connected to the tag and is selected from a group consisting of C3-C16 alkyl group, C3-C16 alkenyl group, and C3-C16 alkynyl group,
wherein one, two or three carbon atoms in formula (I) is/are optionally be substituted with a heteroatom selected from a group consisting of O, S and N,
and wherein one, two, three or four hydrogen atoms in formula (I) is/are optionally be substituted with a group independently selected from hydroxyl group, carboxyl group, amino group, C1-C4 alkoxy group, C1-C4 ether group, C1-C4 thioether group, nitro group, nitrile group, C1-C4 ester group, phenyl group, pyridinyl group, pyrimidinyl group, furanyl group, pyrrolyl group, thiophenyl group, imidazolyl group, and thiazoly group;

each of A, B and Z is independently selected from a group consisting of hydrogen group, C1-C4 alkyl group, amino group, and C1-C4 alkoxy group, wherein the amino group is $NR'_2$, and R' is selected from H and C1-C4 alkyl group.

6. The genetic probe of claim 1, wherein the marker is a transition metal-based fluorescent marker wherein the transition metal-based fluorescent marker is a complex of a transition metal with an aromatic ligand or a chelating carboxylate-based ligand.

7. A kit comprising:
the genetic probe of claim 1;
a first standard target nucleic acid for use as a standard in a calibration, wherein the first standard target nucleic acid comprises a single nucleotide polymorphism (SNP) or a single nucleotide modification to be analysed; and
a second standard target nucleic acid for use as a standard in calibration, wherein the second standard target nucleic acid does not comprise the SNP or the single nucleotide modification to be analysed.

* * * * *